(12) United States Patent
Du et al.

(10) Patent No.: US 7,764,891 B2
(45) Date of Patent: Jul. 27, 2010

(54) SOLID-CONCENTRATION MEASURING APPARATUS AND METHOD THEREOF, AND SOLID-CONCENTRATION CONTROL SYSTEM

(75) Inventors: Jiyun Du, Ishikawa (JP); Satoshi Miyamoto, Ishikawa (JP); Yoshiro Kawamoto, Ishikawa (JP); Seiichi Takeda, Ishikawa (JP); Naoaki Shima, Ishikawa (JP); Shintaro Shitahira, Ishikawa (JP); Norihiro Yamasaku, Ishikawa (JP)

(73) Assignee: PFU Limited (JP)

( * ) Notice: Subject to any disclaimer, the term of this patent is extended or adjusted under 35 U.S.C. 154(b) by 390 days.

(21) Appl. No.: 11/758,482

(22) Filed: Jun. 5, 2007

(65) Prior Publication Data
US 2007/0286626 A1    Dec. 13, 2007

(30) Foreign Application Priority Data
Jun. 7, 2006 (JP) .............................. 2006-158872
Apr. 23, 2007 (JP) .............................. 2007-113365

(51) Int. Cl.
   *G03G 15/10* (2006.01)
(52) U.S. Cl. ............................... 399/62; 399/30; 399/57
(58) Field of Classification Search .................. 399/30, 399/57, 58, 62; 73/61.41, 61.49, 61.71, 61.75, 73/64.53, 597, 602
See application file for complete search history.

(56) References Cited

U.S. PATENT DOCUMENTS

| 5,473,934 A | * | 12/1995 | Cobb ........................ 73/61.49 |
| 5,569,844 A | * | 10/1996 | Sowerby .................... 73/61.75 |
| 6,687,477 B2 | * | 2/2004 | Ichida et al. ................ 399/237 |

FOREIGN PATENT DOCUMENTS

| JP | 2003-270959 A | 9/2003 |
| JP | 2005-308855 A | 11/2005 |

\* cited by examiner

*Primary Examiner*—David P Porta
*Assistant Examiner*—Benjamin Schmitt
(74) *Attorney, Agent, or Firm*—Lowe Hauptman Ham & Berner, LLP

(57) ABSTRACT

A solid-concentration measuring apparatus includes an ultrasonic transmitter, an ultrasonic receiver, and a response-time integrator. The ultrasonic transmitter transmits a single-pulse ultrasonic wave to a liquid toner. The ultrasonic receiver receives the single-pulse ultrasonic wave. The ultrasonic transmitter transmits again a single-pulse ultrasonic wave after a predetermined time has passed from when the ultrasonic receiver receives the single-pulse ultrasonic wave. The response-time integrator measures a response time from transmission to reception of each single-pulse ultrasonic wave, and integrates the response time with respect to each set of N pulses (N>1). A solid concentration of the liquid toner is calculated based on the integrated response time.

17 Claims, 12 Drawing Sheets

| | T1 | T2 | T3 | T4 |
|---|---|---|---|---|
| X1 | $S_{11}$ | $S_{12}$ | $S_{13}$ | $S_{14}$ |
| X2 | $S_{21}$ | $S_{22}$ | $S_{23}$ | $S_{24}$ |
| X3 | $S_{31}$ | $S_{32}$ | $S_{33}$ | $S_{34}$ |
| X4 | $S_{41}$ | $S_{42}$ | $S_{43}$ | $S_{44}$ |

TEMPERATURE TABLE

TEMPERATURE: CONSTANT

| $S_{11}$ | $S_{12}$ | $S_{13}$ | $S_{14}$ | $S_{21}$ | $S_{22}$ | $S_{23}$ | |
|---|---|---|---|---|---|---|---|
| C1 | C2 | C3 | C4 | C5 | C6 | C7 | |

SOLID CONCENTRATION TABLE

SOLID-CONCENTRATION MEASURING APPARATUS AND METHOD THEREOF, AND SOLID-CONCENTRATION CONTROL SYSTEM

RELATED APPLICATIONS

The present application is based on, and claims priority from, Japan Application Number 2006-158872, filed Jun. 7, 2006, and Japan Application Number 2007-113365, filed Apr. 23, 2007, the disclosures of which are hereby incorporated by reference herein in their entirety.

BACKGROUND OF THE INVENTION

1. Field of the Invention

The present invention relates to a technology for measuring and controlling solid concentration of a liquid containing solid content.

2. Description of the Related Art

There has been proposed an image forming apparatus that forms an image on a recording medium such as a sheet of paper using a liquid toner. The liquid toner is a liquid containing solid content, that is, a liquid in which particles or the like containing colorants as the solid content are contained in silicone oil (carrier liquid). For the liquid toner, toner concentration (wt %) or solid concentration, which is a ratio of the solid content such as toner particles to the silicone oil, is important. This is because the change in the solid concentration of the liquid toner largely affects the quality of the image formed on the sheet, which makes it difficult to keep the stable quality. Therefore, conventionally, a solid-concentration measuring apparatus that measures solid concentration of a liquid toner is proposed.

A conventional solid-concentration measuring apparatus is disclosed in, for example, Japanese Patent Application Laid-Open No. 2003-270959. The conventional solid-concentration measuring apparatus is configured to provide a solid-concentration measuring apparatus, which includes a concentration detecting roller, in a toner tank and to form a toner layer on the concentration detecting roller with a liquid toner retained in the toner tank. A reflection intensity of the toner layer formed on the concentration detecting roller is detected by an optical sensor, and the solid concentration is measured based on the reflection intensity.

The conventional solid-concentration measuring apparatus, however, measures the solid concentration based on the reflection intensity of the toner layer, and the measurement is thereby largely affected by a state of the toner layer and a surface state of the concentration detecting roller. Because the temperature causes the viscosity of the liquid toner to change, a transfer amount of the liquid toner to the concentration detecting roller changes depending on the temperature. Moreover, a nip pressure of the roller changes caused by variation in precision of components such as the roller. Therefore, it may be impossible to form the toner layer with uniform thickness. Furthermore, the surface of the concentration detecting roller may be changed caused by roller wear. As explained above, the conventional solid-concentration measuring apparatus is affected by these disturbances, and the measurement precision of the solid concentration is thereby insufficient.

SUMMARY OF THE INVENTION

It is an object of the present invention to at least partially solve the problems in the conventional technology.

According to an aspect of the present invention, a solid-concentration measuring apparatus that measures a solid concentration of a liquid containing solid content, includes an ultrasonic transmitter that transmits a first single-pulse ultrasonic wave to the liquid, an ultrasonic receiver that faces the ultrasonic transmitter through the liquid and receives the first single-pulse ultrasonic wave, an ultrasonic-transmission controller that controls the ultrasonic transmitter to transmit a second single-pulse ultrasonic wave after a predetermined time has passed from when the ultrasonic receiver receives the first single-pulse ultrasonic wave, a response-time integrator that measures a response time from transmission to reception of each single-pulse ultrasonic wave and integrates measured response time with respect to each set of N pulses (N>1), and a concentration calculator that calculates the solid concentration based on integrated response time.

According to another aspect of the present invention, a solid-concentration control system includes a toner tank that is configured to contain a liquid toner, a first supply unit that supplies a concentrated liquid toner to the toner tank, a second supply unit that supplies a dilute solution including silicone oil to the toner tank, a supply controller that controls supply of at least one of the concentrated liquid toner and the dilute solution to the toner tank, and a solid-concentration measuring apparatus that measures a solid concentration of the liquid toner contained in the toner tank. The solid-concentration measuring apparatus includes an ultrasonic transmitter that transmits a single-pulse ultrasonic wave to the liquid toner, an ultrasonic receiver that faces the ultrasonic transmitter through the liquid toner, and that receives the single-pulse ultrasonic wave, an ultrasonic-transmission controller that controls the ultrasonic transmitter to transmit another single-pulse ultrasonic wave after a predetermined time has passed after the ultrasonic receiver receives the single-pulse ultrasonic wave, a response-time integrator that measures a response time from transmission to reception of each single-pulse ultrasonic wave, and integrates measured response time with respect to each set of N pulses (N>1), and a concentration calculator that calculates the solid concentration based on integrated response time. The liquid toner includes color particles as solid content and silicone oil as a carrier liquid. The supply controller controls the supply to the toner tank based on measured solid concentration of the liquid toner to adjust the solid concentration to a predetermined concentration.

According to still another aspect of the present invention, a solid-concentration measuring method for measuring a solid concentration of a liquid containing solid content, includes transmitting a first single-pulse ultrasonic wave to the liquid, receiving the first single-pulse ultrasonic wave, transmitting a second single-pulse ultrasonic wave after a predetermined time has passed from receipt of the single-pulse ultrasonic wave, measuring a response time from transmission to reception of each single-pulse ultrasonic wave, integrating measured response time with respect to each set of N pulses (N>1), and calculating the solid concentration based on integrated response time.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention are explained in detail below with reference to the accompanying drawings. It should be noted that the present invention is not restricted to the following embodiments. Components explained in the following embodiments include those conventionally known or those can be developed in the art hereafter. In the following embodiments, as a liquid containing solid content, a liquid toner is explained below, but the present invention is not limited thereto. More specifically, the liquid toner uses silicone oil, as a carrier liquid, containing toner particles which are particles containing at least colorants. The liquid toner is supplied to an image forming apparatus that forms an image on a recording medium, for example, a sheet of paper. The image forming apparatus includes those which can form an image on a recording medium such as a printer, and a copier.

Figure 1:
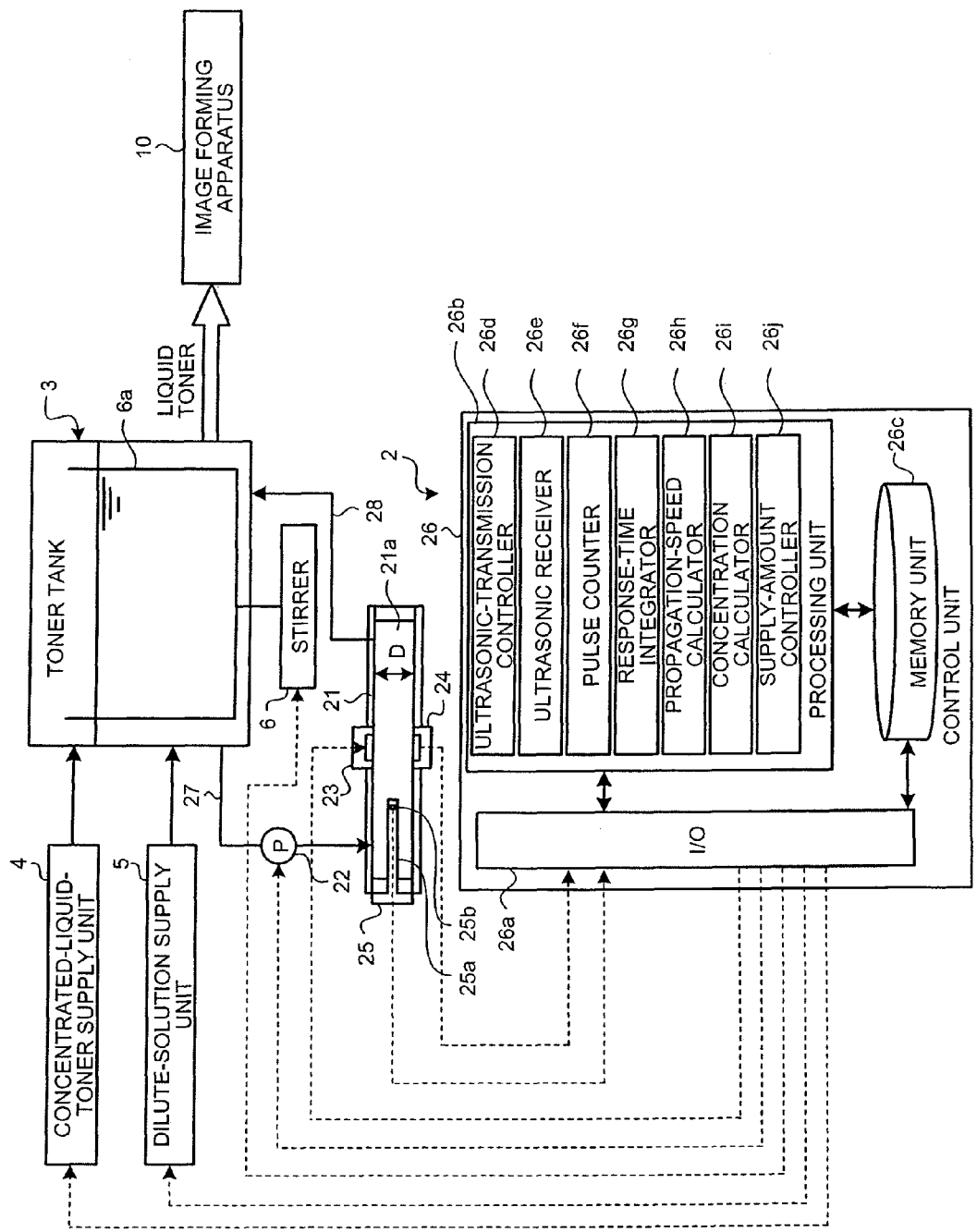
FIG. 1 is a schematic diagram of a solid-concentration control system that includes a solid-concentration measuring apparatus according to a first embodiment of the present invention.
Figures 2, 3:
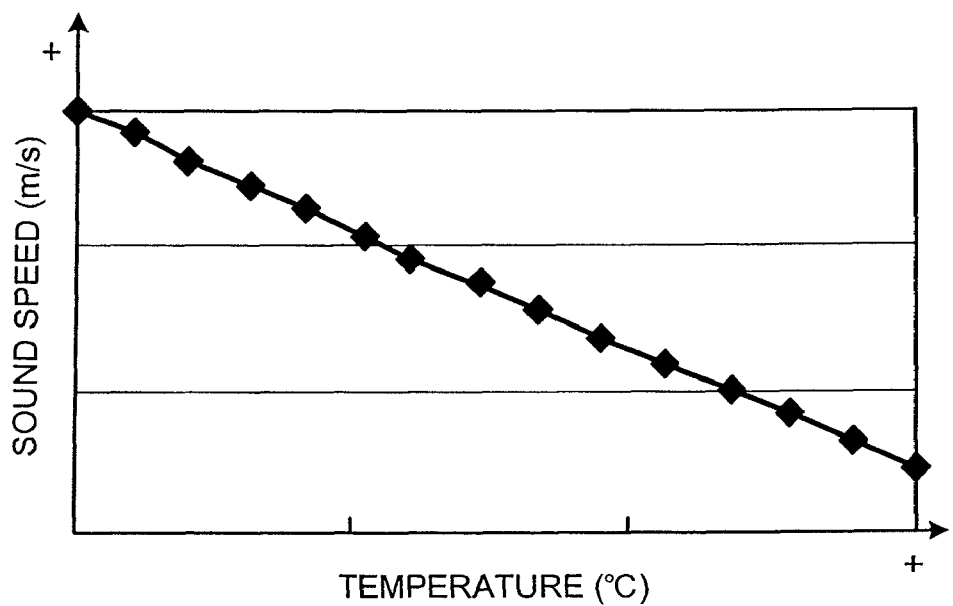
FIG. 2 is a graph of a relation between sound speed and temperature.
FIG. 3 is an example of contents of a temperature table.
Figures 4, 5:
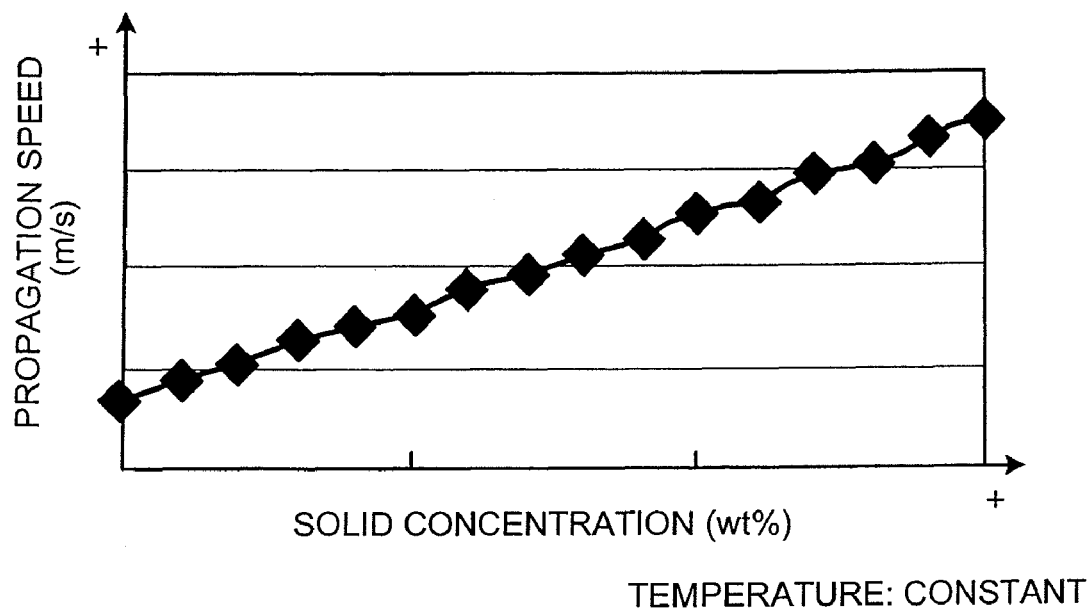
FIG. 4 is a graph of a relation between propagation speed and solid concentration.
FIG. 5 is an example of contents of a solid concentration table.

FIG. 1 is a schematic diagram of a solid-concentration control system 1-1 according to a first embodiment of the present invention. FIG. 2 is a graph of a relation between sound speed and temperature. FIG. 3 is an example of contents of a temperature table. FIG. 4 is a graph of a relation between propagation speed and solid concentration. FIG. 5 is an example of contents of a solid concentration table.

As shown in FIG. 1, the solid-concentration control system 1-1 includes a solid-concentration measuring apparatus 2, a toner tank 3, a concentrated-liquid-toner supply unit 4, and a dilute-solution supply unit 5.

The solid-concentration measuring apparatus 2 measures solid concentration of a liquid toner retained in the toner tank 3 in the first embodiment. The solid-concentration measuring apparatus 2 includes a solid-concentration measuring unit 21, a circulation pump 22, an ultrasonic transmitter 23, an ultrasonic sensor 24, a temperature sensor 25, a control unit 26, and circulation tubes 27 and 28.

The solid-concentration measuring unit 21 circulates a liquid toner supplied from the toner tank 3 between the ultrasonic transmitter 23 and the ultrasonic sensor 24. The solid-concentration measuring unit 21 is provided separately from the toner tank 3. The solid-concentration measuring unit 21 according to the first embodiment is a cylindrical shape with a space 21a formed therein. The space 21a is shielded at its both ends in the longitudinal direction. The space 21a communicates with each one end of the circulation tubes 27 and 28 near the both ends. The other ends of the circulation tubes 27 and 28 communicate with the toner tank 3, respectively. In other words, the solid-concentration measuring unit 21 communicates with the toner tank 3 through the circulation tubes 27 and 28.

The circulation pump 22 circulates the liquid toner between the toner tank 3 and the solid-concentration measuring unit 21. The circulation pump 22 is disposed at a midpoint of the circulation tube 27 in the first embodiment. Therefore, by driving the circulation pump 22, the liquid toner in the toner tank 3 is sucked by the circulation pump 22 through the circulation tube 27. The liquid toner discharged from the circulation pump 22 is supplied to the space 21a in the solid-concentration measuring unit 21 through the circulation tube 27. The liquid toner supplied to the space 21a is returned to the toner tank 3 through the circulation tube 28. Drive or stop of the circulation pump 22 is controlled by the control unit 26.

The ultrasonic transmitter 23 includes an impulse transducer (not shown) that transmits an ultrasonic wave, and a drive circuit that applies a transmission drive voltage to the impulse transducer. The ultrasonic transmitter 23 is disposed in the solid-concentration measuring unit 21 so that the impulse transducer transmits an ultrasonic wave toward the liquid toner passing through the space 21a in the solid-concentration measuring unit 21. Ultrasonic transmission of the ultrasonic transmitter 23 is controlled by an ultrasonic-transmission controller 26d, explained later, of the control unit 26.

The ultrasonic sensor 24 is an ultrasonic receiver, which includes an impulse transducer (not shown) that receives ultrasonic waves. The ultrasonic sensor 24 is disposed in the solid-concentration measuring unit 21, facing the ultrasonic transmitter 23 through the space 21a in the solid-concentration measuring unit 21. In other words, the ultrasonic sensor 24 faces the ultrasonic transmitter 23 through the liquid toner.

When receiving the ultrasonic wave, the ultrasonic sensor 24 outputs a received voltage to the control unit 26. Because the liquid toner circulates between the toner tank 3 and the solid-concentration measuring unit 21, accumulation of the toner in the space 21a and fixation of the toner to the ultrasonic transmitter 23 and the ultrasonic sensor 24 can be suppressed. Consequently, it is possible to minimize the decrease in the measurement precision of the toner concentration of the liquid toner or of the solid concentration of the liquid containing solid content.

The temperature sensor 25 is a temperature detector that detects a temperature T of the liquid toner. The temperature sensor 25 is fixed to one end of the space 21a in the solid-concentration measuring unit 21 in the longitudinal direction. The temperature sensor 25 includes a probe 25a and a platinum temperature sensor 25b. The probe 25a is a cylindrical shape, and the platinum temperature sensor 25b is provided near the end of the probe 25a. The probe 25a of the temperature sensor 25 is inserted into the space 21a, so that the platinum temperature sensor 25b is located near the ultrasonic transmitter 23 and the ultrasonic sensor 24. Because the platinum temperature sensor 25b is provided near the end of the probe 25a, it is possible to suppress the effect of external temperature of the solid-concentration measuring unit 21 on the platinum temperature sensor 25b. Moreover, because the platinum temperature sensor 25b is located near the ultrasonic transmitter 23 and the ultrasonic sensor 24, it is possible to detect the temperature of the liquid toner through which the ultrasonic wave propagates, or the temperature of the liquid toner between the ultrasonic transmitter 23 and the ultrasonic sensor 24. With these features, the temperature sensor 25 can detect the temperature T of the liquid toner with high precision.

The control unit 26 controls the operation of the solid-concentration control system 1-1 that includes the solid-concentration measuring apparatus 2, and implements the solid-concentration control process to which is applied the solid-concentration measuring method. Input into the control unit 26 are the received voltage of the ultrasonic wave received by the ultrasonic sensor 24 and the temperature detected by the temperature sensor 25. The control unit 26 calculates the solid concentration from the input data, and from a temperature table and a solid concentration table, explained later, stored in a memory unit 26c. The control unit 26 further controls the concentrated-liquid-toner supply unit 4 to supply concentrated liquid toner to the toner tank 3 and also controls the dilute-solution supply unit 5 to supply the dilute solution to the toner tank 3, based on the calculated solid concentration.

The control unit 26 includes an input-output (I/O) unit 26a, a processing unit 26b, and the memory unit 26c. The processing unit 26b is formed with a memory and a central processing unit (CPU). The processing unit 26b includes an ultrasonic-transmission controller 26d, an ultrasonic receiver 26e, a pulse counter 26f, a response-time integrator 26g, a propagation-speed calculator 26h, a concentration calculator 26i, and a supply-amount controller 26j.

The processing unit 26b can load a computer program (hereinafter, "solid-concentration control program") into the memory and execute it to implement the solid-concentration control process to which is applied the solid-concentration measuring method explained later. The memory unit 26c can be formed with a nonvolatile memory such as a flash memory, a memory that can only read data such as a read only memory (ROM), or a memory that can read and write data such as a random access memory (RAM), or a combination of these memories. The memory unit 26c stores therein the temperature table and the solid concentration table.

The ultrasonic-transmission controller 26d causes the ultrasonic transmitter 23 to transmit each ultrasonic pulse. The transmission allows a transmission circuit of the ultrasonic transmitter 23 to apply a transmission drive voltage for one pulse to the impulse transducer, and the impulse transducer thereby transmits one ultrasonic pulse.

The ultrasonic receiver 26e determines whether one ultrasonic pulse transmitted from the ultrasonic transmitter 23 has been received based on the received voltage of the ultrasonic wave which is output to the control unit 26 and received by the ultrasonic sensor 24.

The pulse counter 26f counts a pulse each time one ultrasonic pulse is transmitted from the ultrasonic transmitter 23.

The response-time integrator 26g measures a response time t for each pulse, the response time t being from transmission of one ultrasonic pulse by the ultrasonic transmitter 23 to reception of the one ultrasonic pulse by the ultrasonic sensor 24. The response-time integrator 26g integrates the measured response time t for each N pulses (N>1).

The propagation-speed calculator 26h is part of a concentration calculator. The propagation-speed calculator 26h calculates a propagation speed S of the ultrasonic wave from the ultrasonic transmitter 23 to the ultrasonic sensor 24, based on a propagation distance D from the ultrasonic transmitter 23 to the ultrasonic sensor 24, an integrated response time X which is a response time for N pulses integrated by the response-time integrator 26g, and a temperature T detected by the temperature sensor 25. In the first embodiment, the propagation-speed calculator 26h calculates the propagation speed S based on the integrated response time X and the temperature table stored in the memory unit 26c.

A propagation speed (m/s) without consideration of the temperature (° C.) can be calculated by using equation D/(X/N) between the integrated response time X, the propagation distance D, and the number N of pulses to integrate the integrated response time X. As shown in FIG. 2, however, the silicone oil being the liquid of the liquid toner has such a feature that a sound speed in the silicone oil decreases as the temperature of the silicone oil increases. The change in the sound speed in the silicone oil is proportional to the change in the temperature of the silicone oil.

More specifically, the liquid toner which is the liquid containing solid content has a feature such that the propagation speed of the ultrasonic wave changes depending on the temperature T. Therefore, if the temperature T changes even if the integrated response time X is not changed, calculated solid concentrations C are different from each other even if the integrated response time X remains the same.

As shown in FIG. 3, the temperature table is used to calculate an ultrasonic propagation speed S ($S_{11}$, $S_{12}$, $S_{13}$, $S_{14}$, $S_{21}$, . . . ), obtained by removing a change amount of the sound speed in the silicone oil due to the temperature change, from detected temperature T (T1, T2, T3, T4, . . . ) and integrated response time X (X1, X2, X3, X4, . . . ).

The temperature table is set, allowing for a relation between the temperature of and the sound speed in the silicone oil, so that when the integrated response time X is constant and the detected temperature T increases, the ultrasonic propagation speed S (hereinafter, "propagation speed S") increases more than the propagation speed calculated by using the equation D/(X/N), the propagation speed S being obtained by removing the change amount of the sound speed in the silicone oil due to the temperature change therefrom. Moreover, the temperature table is set so that the propagation speed S increases when the detected temperature T is constant and the integrated response time X increases. It is noted that the temperature table can be previously prepared by the solid-concentration measuring apparatus 2, by measuring the propagation speed when the solid concentration C is constant and the temperature T is changed.

As shown in FIG. 1, the propagation-speed calculator 26h calculates the propagation speed S based on the propagation distance D, the integrated response time X, and the detected temperature T, and the concentration calculator 26i calculates the solid concentration C based on the propagation speed S. That is, the propagation-speed calculator 26h corrects the calculated solid concentration C according to the detected change in the temperature T. Consequently, even if the temperature T changes during the measurement of the solid concentration C by the solid-concentration measuring apparatus 2, it can be suppressed that the calculated solid concentration C is different from an actual concentration of the liquid toner. With this feature, it is possible to improve the measurement precision of the solid concentration of the liquid toner or of the solid concentration of the liquid containing the solid content.

The concentration calculator 26i calculates the solid concentration C of the liquid toner which is the liquid containing solid content, based on the integrated response time X or, in this case, based on the propagation speed S calculated by the propagation-speed calculator 26h. In the first embodiment, the concentration calculator 26i calculates the solid concentration C based on the propagation speed S and the solid concentration table stored in the memory unit 26c.

As shown in FIG. 4, the solid concentration C (wt %) increases with an increase in the propagation speed S of the liquid toner. More specifically, the solid concentration C (wt %) is a ratio of the solid content with particles containing colorants to the silicone oil. The change in the solid concentration C is proportional to the change in the propagation speed S in the liquid toner. As shown in FIG. 5, the solid concentration table can be used to calculate a solid concentration C ($C_1$, $C_2$, $C_3$, $C_4$, ...) from the calculated propagation speed S ($S_{11}$, $S_{12}$, $S_{13}$, $S_{14}$, $S_{21}$, ...). The solid concentration table is set so that the solid concentration C increases proportionally to an increase in the calculated propagation speed S, allowing for the relation between the solid concentration C and the propagation speed S. It is noted that the solid concentration table can be previously prepared by the solid-concentration measuring apparatus 2, by measuring the propagation speed S when the temperature T is constant and the solid concentration C is changed.

The supply-amount controller 26j controls the concentrated-liquid-toner supply unit 4 to supply the concentrated liquid toner to the toner tank 3 or the dilute-solution supply unit 5 to supply the dilute solution to the toner tank 3. The supply-amount controller 26j causes the concentrated-liquid-toner supply unit 4 or the dilute-solution supply unit 5 to supply the concentrated liquid toner or the dilute solution to the toner tank 3, based on the solid concentration of the liquid toner measured by the solid-concentration measuring apparatus 2 or the solid concentration C calculated by the concentration calculator 26i so that the solid concentration C becomes a predetermined concentration.

The solid-concentration control program is not necessarily limited by a unique configuration, and can achieve its function in conjunction with another computer program already stored in a computer system, such as a discrete program represented as an operating system (OS). Besides, a computer program stored in a computer-readable recording medium can be loaded into the computer system and executed to realize the same function as the processing unit 26b. In this case, also, the solid-concentration control system 1-1 can control the solid concentration C, and the solid-concentration measuring apparatus 2 can measure the solid concentration C. The computer system includes the OS and hardware such as peripheral.

The toner tank 3 retains therein a liquid toner. The toner tank 3 is connected to an image forming apparatus 10, and the retained liquid toner is appropriately supplied to the image forming apparatus 10.

The concentrated-liquid-toner supply unit 4 supplies a concentrated liquid toner with a solid concentration higher than that of an ordinary liquid toner, to the toner tank 3 in the first embodiment. The concentrated-liquid-toner supply unit 4 includes a concentrated-liquid-toner tank (not shown) for retaining therein the concentrated liquid toner, and a valve for concentrated liquid toner (not shown) for opening/closing a communicating tube in communication with the concentrated-liquid-toner tank and the toner tank 3. The concentrated-liquid-toner supply unit 4 supplies the concentrated liquid toner to the toner tank 3 by opening the valve. It is noted that the supply-amount controller 26j of the control unit 26 controls the opening/closing of the valve or the supply of the concentrated liquid toner.

The dilute-solution supply unit 5 supplies only a low-concentration liquid toner, which has solid concentration lower than that of the ordinary liquid toner, or only the liquid i.e., only the silicone oil, to the toner tank 3 in the first embodiment. The dilute-solution supply unit 5 includes a dilute-solution toner tank (not shown) for retaining therein the dilute solution, and a valve for dilute solution (not shown) for opening/closing a communicating tube in communication with the dilute-solution toner tank and the toner tank 3. The dilute-solution supply unit 5 supplies the dilute solution to the toner tank 3 by opening the valve. It is noted that the supply-amount controller 26j of the control unit 26 controls the opening/closing of the valve i.e., the supply of the dilute solution.

A stirrer 6 stirs the liquid toner retained in the toner tank 3. The stirrer 6 stirs the liquid toner retained therein by operating a stirring blade 6a provided in the toner tank 3, to make uniform the concentration of the liquid toner therein. The liquid toner is stirred when the concentrated liquid toner or the dilute solution is supplied to the toner tank 3. It is noted that the control unit 26 controls the stirring of the liquid toner in the toner tank 3.

Figure 6:
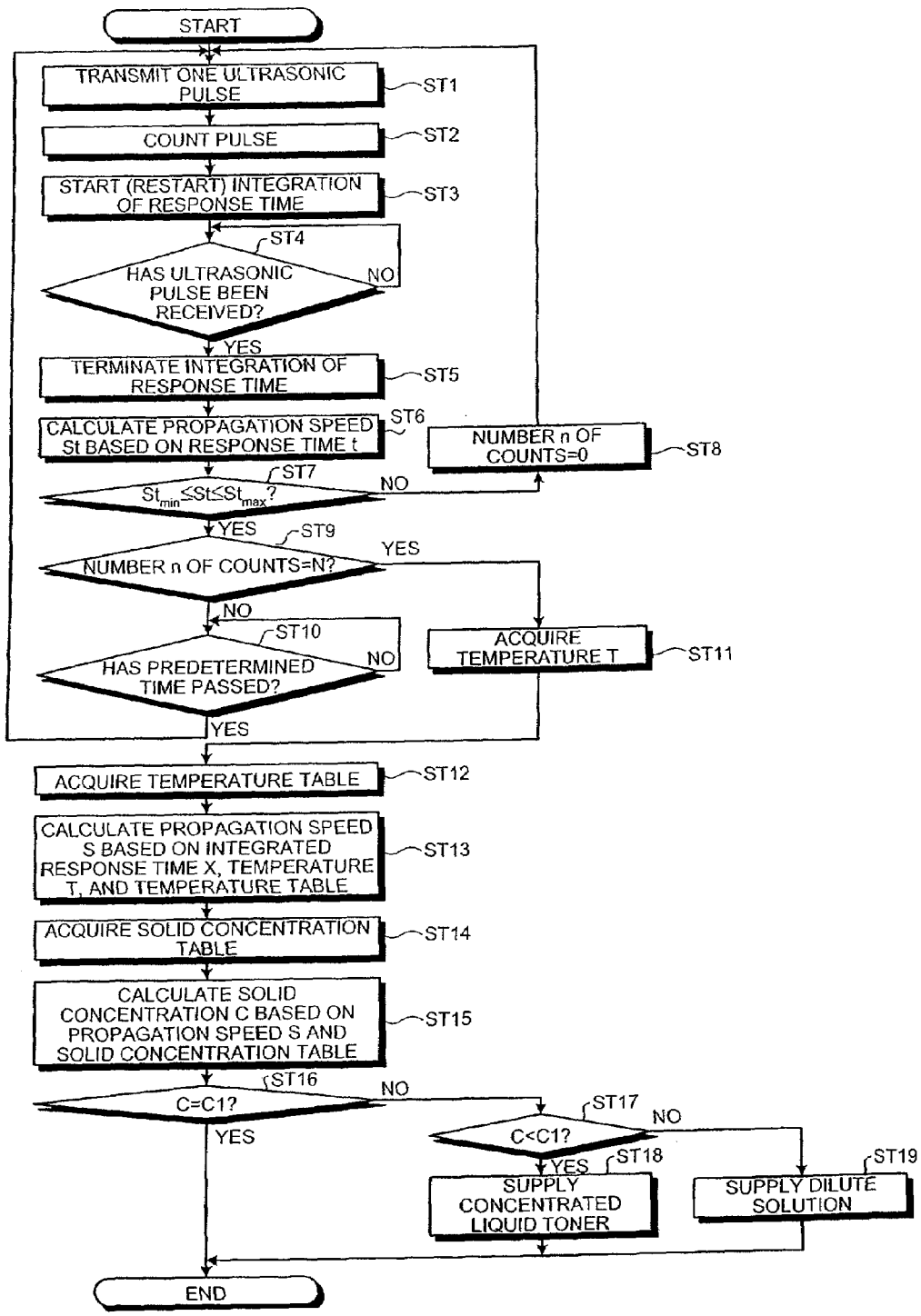
FIG. 6 is a flowchart of a solid-concentration control process to which is applied a solid-concentration measuring method according to the first embodiment.
Figure 7:
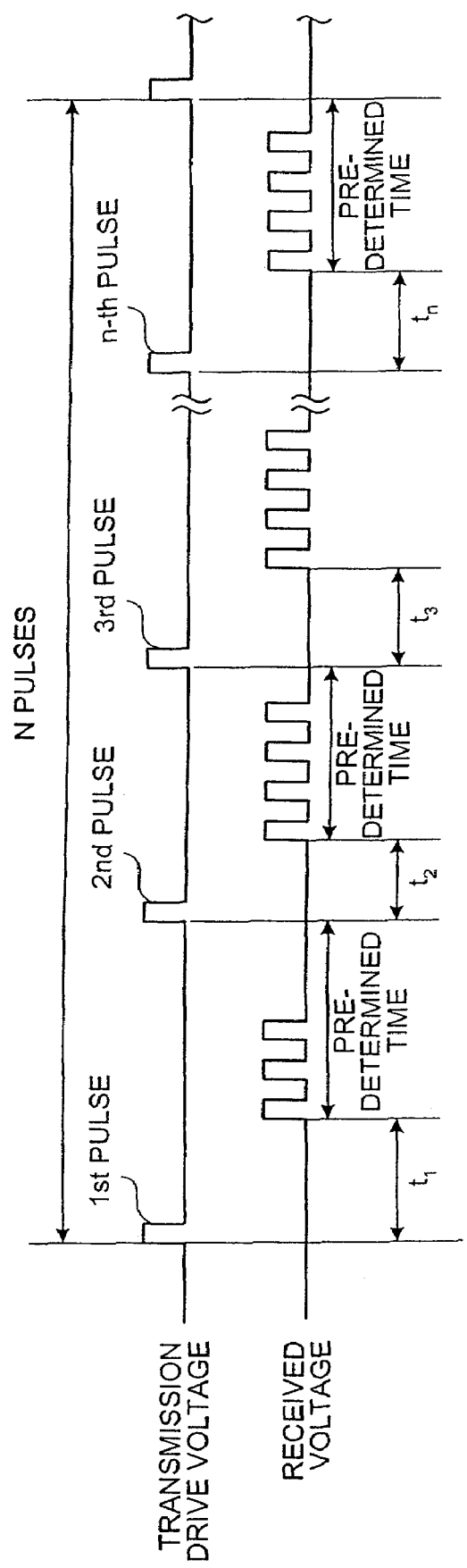
FIG. 7 is a schematic diagram for explaining a relation between a transmission drive voltage and a received voltage.

The operation of the solid-concentration control system 1-1 or the solid-concentration control process to which is applied the solid-concentration measuring method according to the first embodiment is explained below. FIG. 6 is a flowchart of the solid-concentration control process to which is applied the solid-concentration measuring method. FIG. 7 is a schematic diagram for explaining a relation between a transmission drive voltage and a received voltage.

The control unit 26 drives the circulation pump 22 when the image forming apparatus 10 is operated. More specifically, the control unit 26 drives the circulation pump 22 when the solid-concentration control system 1-1 measures the solid concentration C of the liquid toner. The liquid toner is thereby circulated between the toner tank 3 and the solid-concentration measuring unit 21.

The ultrasonic-transmission controller 26d causes the ultrasonic transmitter 23 to transmit one ultrasonic pulse (step ST1). Specifically, the ultrasonic-transmission controller 26d causes the transmission circuit of the ultrasonic transmitter 23 to apply a transmission drive voltage for one pulse to the impulse transducer, and causes the impulse transducer to transmit an ultrasonic pulse toward the liquid toner.

The pulse counter 26f counts a pulse when the ultrasonic pulse is transmitted from the ultrasonic transmitter 23 (step ST2). For example, when a first ultrasonic pulse is transmitted from the ultrasonic transmitter 23, the pulse counter counts the pulse and sets the number n of counts to 1.

The response-time integrator 26g starts integration of response time (step ST3). Specifically, the response-time integrator 26g starts measurement of a response time t when one ultrasonic pulse is transmitted from the ultrasonic transmitter 23.

The ultrasonic receiver 26e determines whether the ultrasonic sensor 24 has received the ultrasonic pulse (step ST4). Specifically, the ultrasonic receiver 26e receives the transmitted one ultrasonic pulse, and thereby determines whether the ultrasonic sensor 24 has received the ultrasonic pulse based on whether the received voltage output to the control unit 26 is a predetermined voltage or higher. It is noted that that the ultrasonic receiver 26e repeats determination as to whether the ultrasonic pulse has been received until it is determined that the ultrasonic sensor 24 has received the ultrasonic pulse.

The response-time integrator 26g terminates the integration of the response time when the ultrasonic receiver 26e has received the ultrasonic pulse (step ST5). Specifically, when the ultrasonic receiver 26e initially receives one ultrasonic pulse after the one ultrasonic pulse is transmitted from the ultrasonic transmitter 23, the response-time integrator 26g terminates the integration of the response time. Consequently, as shown in FIG. 7, the response-time integrator 26g measures a response time t from transmission of one ultrasonic pulse by the ultrasonic transmitter to its reception.

The response-time integrator 26g calculates one-pulse propagation speed St from the calculated response time t (step ST6). At this step, the response-time integrator 26g calculates the propagation speed St for each pulse based on the response time t for each pulse or each time an ultrasonic pulse is transmitted by the ultrasonic transmitter 23.

The response-time integrator 26g determines whether the calculated propagation speed St for each pulse is in a range from the minimum speed $St_{min}$ to the maximum speed $St_{max}$ (step ST7).

When the calculated propagation speed St for each pulse is not in the range, the pulse counter 26f sets the number n of counts to 0 (step ST8). Specifically, the pulse counter 26f resets the number n of counts obtained by counting a pulse each time an ultrasonic pulse is transmitted from the ultrasonic transmitter 23. More specifically, the response-time integrator 26g integrates only the response time from transmission of one ultrasonic pulse by the ultrasonic transmitter to its reception only when the propagation speed St for each pulse based on the response time t from transmission of one ultrasonic pulse to its reception is in a predetermined range or in the range from the minimum speed $St_{min}$ to the maximum speed $St_{max}$.

The liquid toner retained in the toner tank 3 may sometimes contain air bubbles. Generally, the sound speed in a liquid is largely different from that in a gas, and thus, the sound speed in the liquid toner largely changes depending on whether the air bubbles are contained therein. Consequently, the predetermined range is defined as a range that does not include the propagation speed S when the transmitted ultrasonic pulse propagates through the air bubbles and the liquid, or, in this case, through the liquid toner containing air bubbles. Therefore, of calculated propagation speeds S, the response-time integrator 26g uses only a propagation speed within the predetermined range, for calculation of the solid concentration C. More specifically, the propagation speed used for the calculation is within the range of the propagation speed S when the transmitted ultrasonic pulse propagates only through the liquid toner not containing the air bubbles.

Accordingly, it can be suppressed that the calculated solid concentration C is different from an actual solid concentration even if the air bubbles are contained in the liquid toner as an object to be measured during measurement of the solid concentration C by the solid-concentration measuring apparatus 2. Thus, it is possible to improve the measurement precision of the solid concentration of the liquid toner or of the solid concentration of the liquid containing solid content. Further, it is determined whether the propagation speed is in the range from the minimum speed $St_{min}$ to the maximum speed $St_{max}$, or whether the propagation speed is in the predetermined range. This determination is made for each calculated propagation speed St for each pulse, which can reliably remove the response time t through the liquid toner containing air bubbles, from an integrated response time X. With this feature, it is also possible to improve the measurement precision of the solid concentration C of the liquid toner or of the solid concentration of the liquid containing solid content.

When the calculated propagation speed St for each pulse is in the range from the minimum speed $St_{min}$ to the maximum speed $St_{max}$, the pulse counter 26f determines whether the number n of counts is N (step ST9). Specifically, the pulse counter 26f determines whether the number n of counts obtained by pulse counting each time the ultrasonic transmitter 23 transmits an ultrasonic wave is N, or determines whether the ultrasonic transmitter 23 transmits ultrasonic waves for N pulses. It is noted that N is a value greater than 1, for example, a value ranging from about tens to hundreds of pulses.

When the pulse counter 26f determines that the number n of counts is not N, the ultrasonic-transmission controller 26d determines whether a predetermined time has passed from when it was determined that the ultrasonic receiver 26e had received the ultrasonic wave (step ST10). Specifically, when the number of transmission times of one ultrasonic pulse by the ultrasonic transmitter 23 does not reach N times or when the ultrasonic wave is not transmitted for N pulses by the ultrasonic transmitter 23, the ultrasonic-transmission controller 26d determines whether the predetermined time has passed from when it was determined that the ultrasonic receiver 26e had received the ultrasonic wave. The "predetermined time" indicates a time from when one ultrasonic pulse is transmitted until the ultrasonic sensor 24 receives no more reverberation of at least transmitted one ultrasonic pulse. It is noted that the ultrasonic-transmission controller 26d repeats the determination until it is determined that the predetermined time has passed since it has been determined that the ultrasonic receiver 26e has received the ultrasonic wave.

The ultrasonic transmitter 23 transmits each ultrasonic pulse as explained later. When one ultrasonic pulse is transmitted from the ultrasonic transmitter 23, the reverberation of the ultrasonic pulse occurs between the ultrasonic transmitter 23 and the ultrasonic sensor 24 in the space 21a. As shown in FIG. 7, the ultrasonic sensor 24 receives the transmitted ultrasonic pulse and then outputs a received voltage of a predetermined voltage or more to the control unit 26 because the reverberation of the ultrasonic pulse is determined as if the ultrasonic pulse has been received. Consequently, the response-time integrator 26g cannot accurately measure the response time when the reverberation occurs because even if the ultrasonic transmitter 23 transmits one ultrasonic pulse, the ultrasonic sensor 24 receives the reverberation of the ultrasonic pulse.

However, the ultrasonic-transmission controller 26d does not transmit another one ultrasonic pulse during a period from when the ultrasonic sensor 24 initially receives one ultrasonic pulse after transmission of the one ultrasonic pulse by the ultrasonic transmitter 23 until the ultrasonic sensor 24 receives no more reverberation of at least the transmitted one ultrasonic pulse. Therefore, it is possible to accurately measure a response time t for each transmitted one ultrasonic pulse. Accordingly, the integrated response time X can be accurately calculated, and the propagation speed calculated based on the calculated integrated response time X can be precisely calculated. Thus, it is possible to improve the measurement precision of the solid concentration C of the liquid toner or of the solid concentration of the liquid containing solid content.

When the predetermined time has passed from when it was determined that the ultrasonic receiver 26e had received the ultrasonic wave, the ultrasonic-transmission controller 26d repeats the following processes until the pulse counter 26f determines that the number n of counts is N (step ST9). More specifically, under control of the ultrasonic-transmission controller 26d, the ultrasonic transmitter 23 transmits another one ultrasonic pulse (step ST1). The pulse counter 26f counts a pulse (step ST2). The response-time integrator 26g restarts integration of the response time (step ST3). The response-time integrator 26g terminates again the integration of the response time (step ST5) when the ultrasonic receiver 26e determines that the ultrasonic sensor 24 has received the ultrasonic wave (step ST4). The response-time integrator 26g calculates one-pulse propagation speed St (step ST6). The response-time integrator 26g determines whether the calculated one-pulse propagation speed St is in the range from the minimum speed $St_{min}$ to the maximum speed $St_{max}$.

Consequently, the integrated response time X, which is the response time integrated by the response-time integrator 26g, is the total of response times $t_1$ to $t_n$ from a first pulse to an n-th pulse, each of which is a response time t in the liquid toner not containing air bubbles, as shown in FIG. 7.

As shown in FIG. 6, the propagation-speed calculator 26h acquires a temperature T when the number n of counts is N (step ST11). Specifically, the propagation-speed calculator 26h acquires the temperature T of the liquid toner detected by the temperature sensor 25 and output to the control unit 26.

Next, the propagation-speed calculator 26h acquires the temperature table (step ST12). Specifically, the propagation-speed calculator 26h acquires the temperature table, as shown in FIG. 3, stored in the memory unit 26c.

The propagation-speed calculator 26h calculates the propagation speed S based on the integrated response time X, the temperature T, and the temperature table (step ST13). More specifically, the propagation-speed calculator 26h which is part of a concentration measuring unit calculates the propagation speed S based on the propagation distance D, the integrated response time X, and the detected temperature T by using the temperature table.

The concentration calculator 26i acquires the solid concentration table (step ST14). Specifically, the concentration calculator 26i acquires the solid concentration table, as shown in FIG. 5, stored in the memory unit 26c.

Next, the concentration calculator 26i calculates a solid concentration C based on the propagation speed S when the temperature is constant and the solid concentration table (step ST15). More specifically, the concentration calculator 26i which is the concentration measuring unit calculates the solid concentration C of the liquid toner based on the integrated response time X, that is, based on the propagation distance D and the integrated response time by using the solid concentration table.

As explained above, the solid concentration C can be calculated based on the integrated response time X obtained by integrating a response time t, for N pulses, from transmission of one ultrasonic pulse from the ultrasonic transmitter 23 to its reception by the ultrasonic sensor 24. Alternatively, the solid concentration C can be calculated based on the propagation speed S calculated based on the propagation distance D and the integrated response time X. Therefore, there is no need to consider the effect of disturbance on the case where the solid concentration of the liquid toner is measured by using a conventional optical sensor, and thus, it is possible to improved the measurement precision of the solid concentration C of the liquid toner or of the solid concentration of the liquid containing the solid content.

If the propagation distance D is short, for example, about several millimeters, the change amount of the response time t corresponding to the change in the solid concentration of the liquid toner becomes a slight amount, but the solid-concentration measuring apparatus 2 calculates the solid concentration C based on the integrated response time X obtained by integrating the response time t for N pulses. Consequently, when the solid concentration C changes, the change amount of the integrated response time X can be set to N times of the change amount of the response time t. Therefore, the change in the integrated response time X can be measured more accurately than the change in the response time t. With this feature, there is no need to provide components with high measurement precision even if the propagation distance D is short, and thus, the measurement precision of the solid concentration C can be improved.

The supply-amount controller 26j determines whether the calculated solid concentration C is a predetermined concentration C1 (step ST16). The term "predetermined concentration C1" as used herein refers to concentration with which the quality of the toner image transferred to the recording medium by the image forming apparatus 10 can be stably maintained. The predetermined concentration C1 may be stored in the previously set memory unit 26c, or may be set by the user for each operation of the image forming apparatus 10. More specifically, the supply-amount controller 26j determines whether the solid concentration C of the liquid toner retained in the toner tank 3 is an appropriate solid concentration with which the quality of the toner image transferred to the recording medium by the image forming apparatus 10 can be stably maintained. The solid-concentration control system 1-1 ends the operation of one control cycle when the supply-amount controller 26j determines that the solid concentration C calculated by the concentration calculator 26i is the predetermined concentration C1.

Next, when it is determined that the calculated solid concentration C is not the predetermined concentration C1, the supply-amount controller 26j further determines whether the solid concentration C is less than C1 (step ST17). Specifically, the supply-amount controller 26j determines whether the calculated solid concentration C is thinner than the predetermined concentration C1.

When the calculated solid concentration C is less than the predetermined concentration C1, the supply-amount controller 26j supplies the concentrated liquid toner to the toner tank 3 (step ST18). Specifically, the supply-amount controller 26j controls the concentrated-liquid-toner supply unit 4 to supply the concentrated liquid toner, to open the valve for the concentrated liquid toner (not shown). Then, the concentrated-liquid-toner supply unit 4 supplies the concentrated liquid toner retained in the concentrated-liquid-toner tank (not shown) to the toner tank 3. It is noted that the supply amount of the concentrated liquid toner by the concentrated-liquid-toner supply unit 4 may be made constant or may be changed based on the difference between the calculated solid concentration C and the predetermined concentration C1.

When the calculated solid concentration C is the predetermined concentration C1 or higher, the supply-amount controller 26j supplies the dilute solution to the toner tank 3 (step ST19). Specifically, the supply-amount controller 26j controls the dilute-solution supply unit 5 to supply a dilute solution, to open the valve for the dilute solution (not shown). Then the dilute solution supply unit 5 supplies the dilute solution retained in a dilute solution tank (not shown) to the toner tank 3. It is noted that the supply amount of the dilute solution by the dilute-solution supply unit 5 may be made constant or may be changed based on the difference between the calculated solid concentration C and the predetermined concentration C1.

As explained above, the solid-concentration control system 1-1 can easily keep the solid concentration C to the predetermined concentration C1 because the measurement precision of the solid concentration C of the liquid toner measured by the solid-concentration measuring apparatus 2 is high. Therefore, the liquid toner with a desired solid concentration C can be supplied to the image forming apparatus 10. Accordingly, the image forming apparatus 10 enables the stable quality of the toner image on the recording medium to be maintained.

In the first embodiment, the solid-concentration measuring apparatus 2 measures the solid concentration C of the liquid toner in the toner tank 3. However, the present invention is not so limited. For example, the solid-concentration measuring unit 21 of the solid-concentration measuring apparatus 2 may be disposed between the toner tank 3 and the image forming apparatus 10. In other words, the solid-concentration measuring apparatus 2 may also measure the solid concentration of the liquid toner supplied from the toner tank 3 to the image forming apparatus 10.

Figure 8:
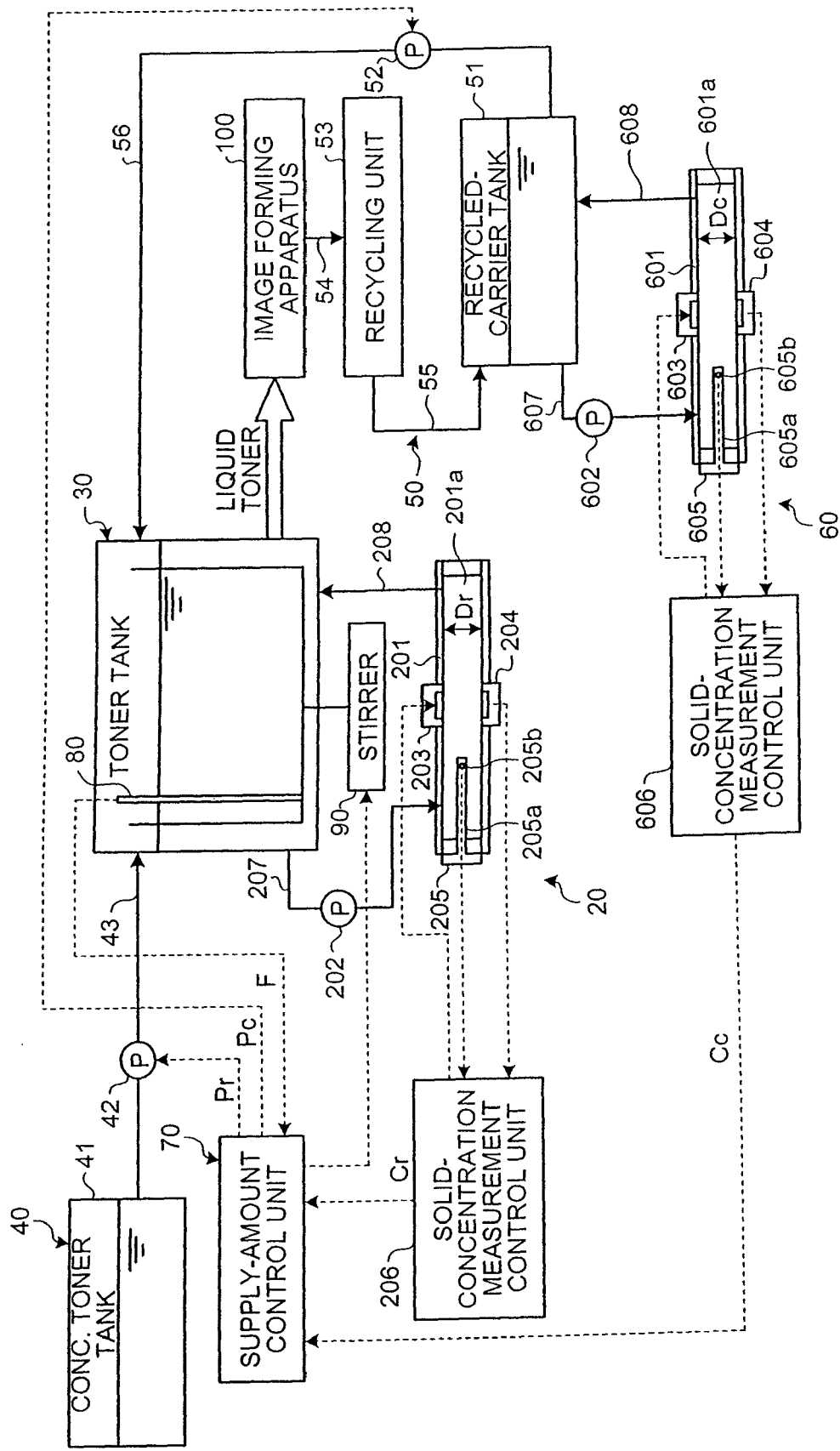
FIG. 8 is a schematic diagram of a solid-concentration control system that includes solid-concentration measuring apparatuses according to a second embodiment of the present invention.
Figure 9:
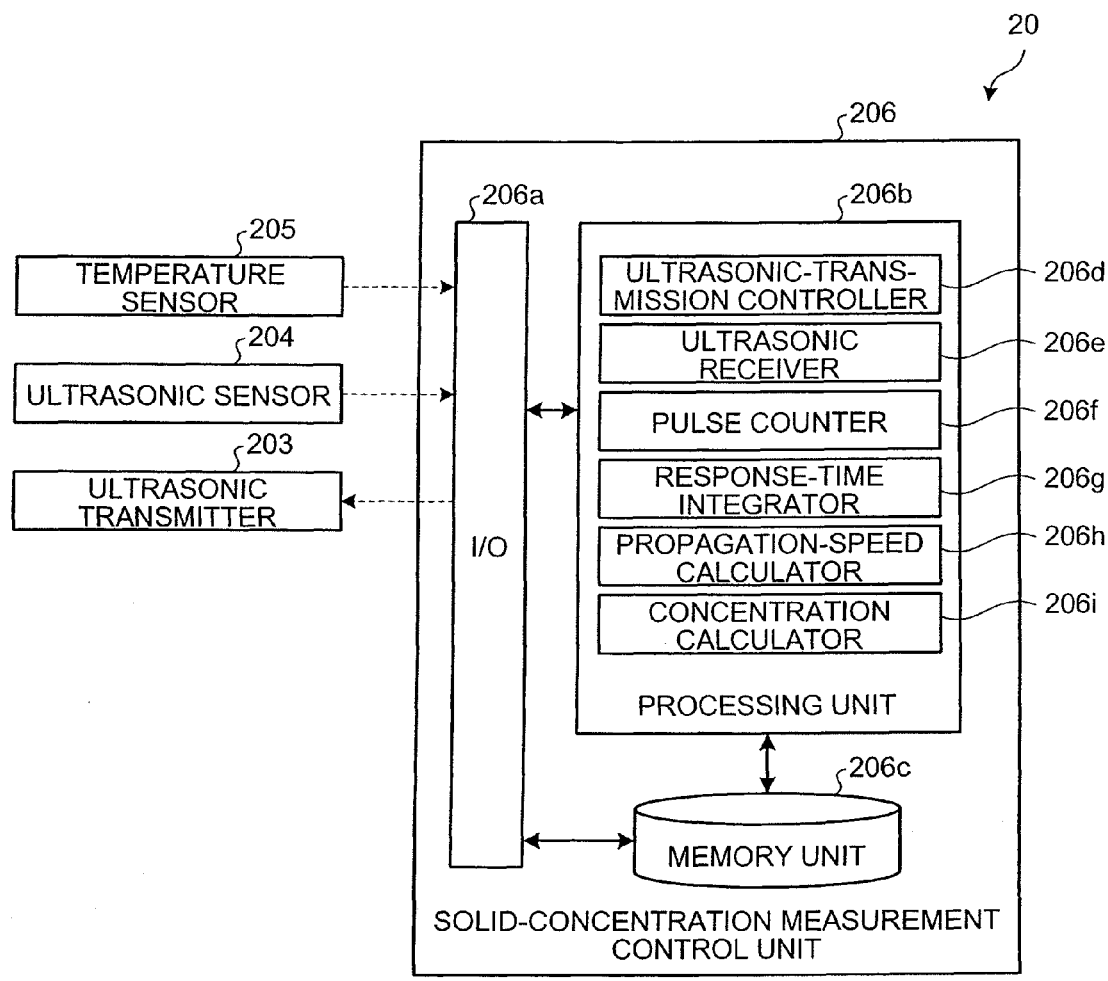
FIG. 9 is a block diagram of a solid-concentration measurement control unit in a solid-concentration measuring apparatus for a liquid toner shown in FIG. 8.
Figure 10:
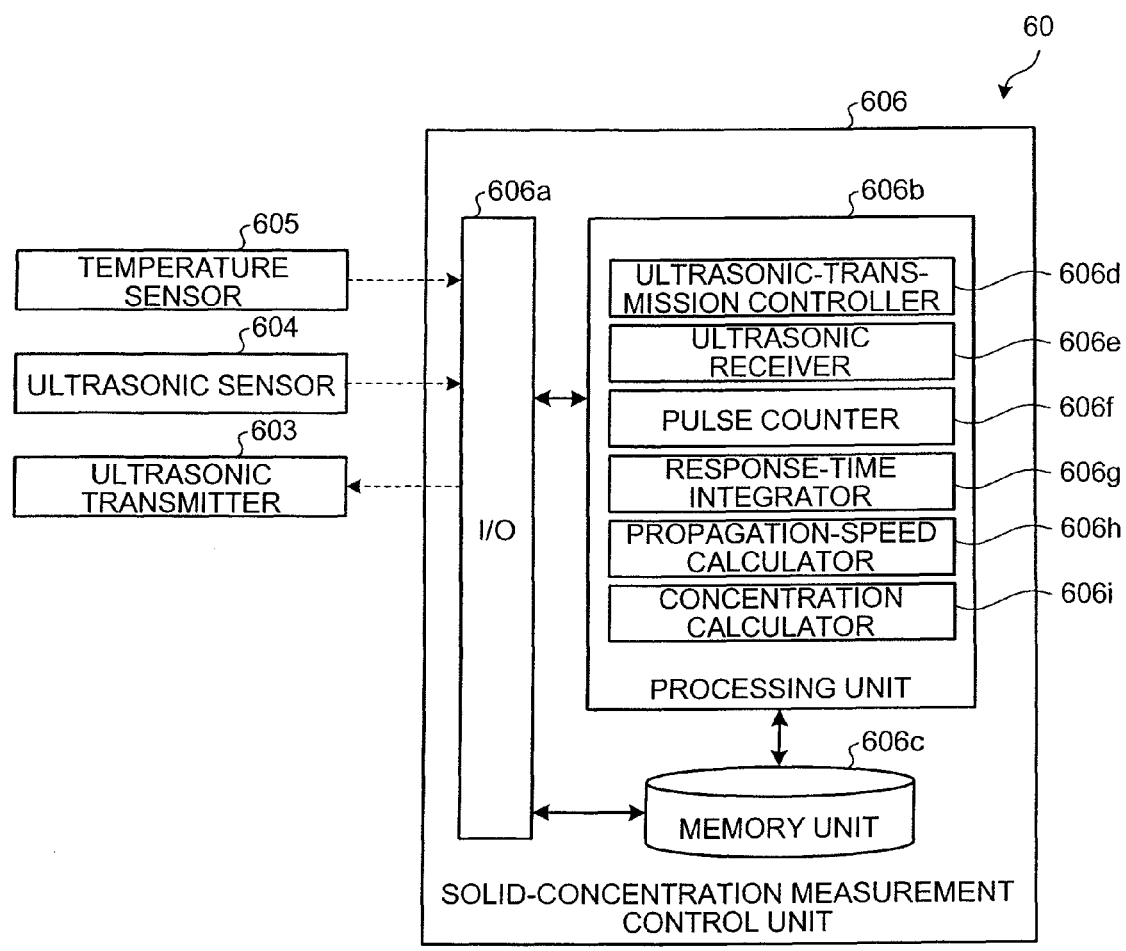
FIG. 10 is a block diagram of a solid-concentration measurement control unit in a solid-concentration measuring apparatus for a dilute solution shown in FIG. 8.
Figure 11:
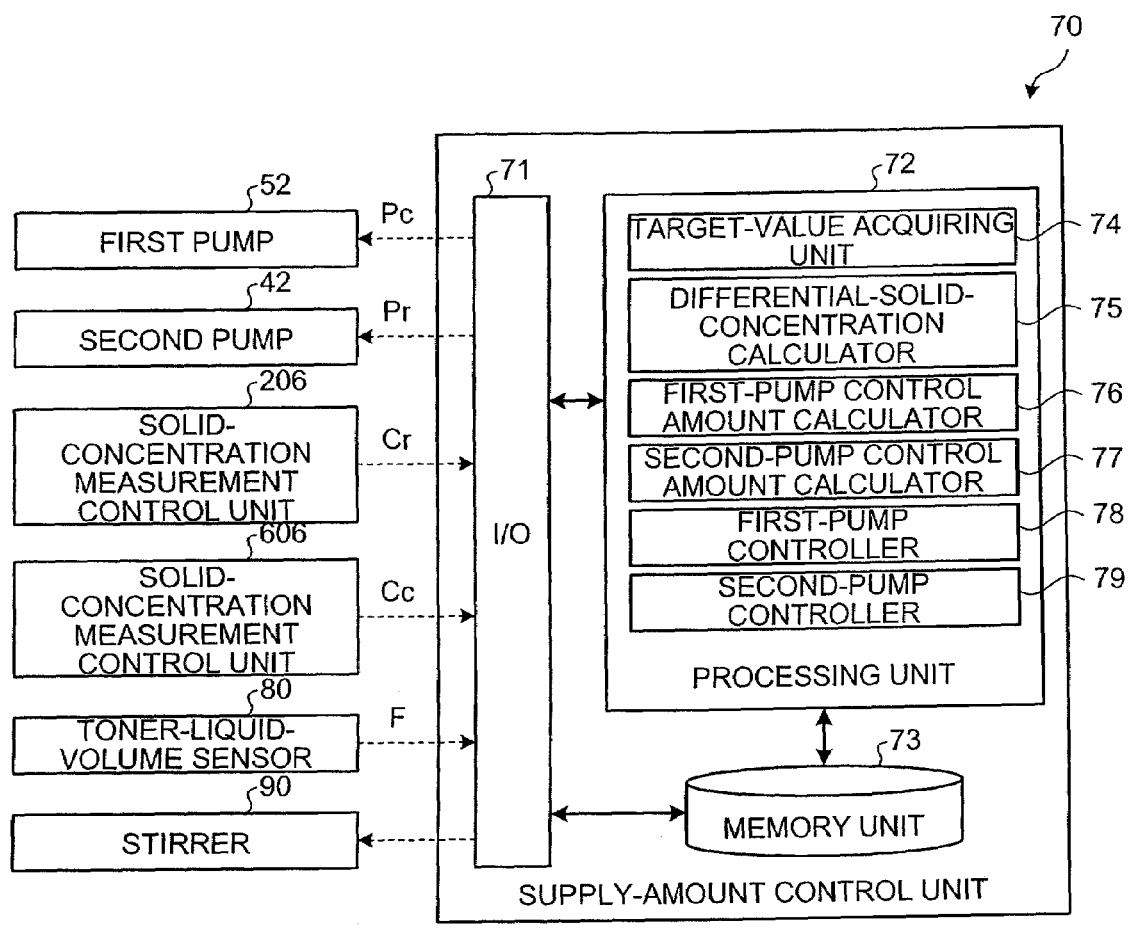
FIG. 11 is a block diagram of a supply-amount control unit shown in FIG. 8.

FIG. 8 is a schematic diagram of a solid-concentration control system 1-2 that includes solid-concentration measuring apparatuses according to a second embodiment of the present invention. FIG. 9 is a block diagram of a solid-concentration measurement control unit in a solid-concentration measuring apparatus for a liquid toner. FIG. 10 is a block diagram of a solid-concentration measurement control unit in a solid-concentration measuring apparatus for a dilute solution. FIG. 11 is a block diagram of a supply-amount control unit. Components, of the basic configuration of the solid-concentration control system 1-2, which are the same or almost the same as the components of the basic configuration of the solid-concentration control system 1-1 according to the first embodiment are omitted or briefly explained.

As shown in FIG. 8, the solid-concentration control system 1-2 includes a solid-concentration measuring apparatus 20 for a liquid toner, a toner tank 30, a concentrated-toner (conc. toner) supply unit 40, a recycled-carrier supply unit 50, a solid-concentration measuring apparatus 60 for a dilute solution, a supply-amount control unit 70, a toner-liquid-volume sensor 80, and a stirrer 90.

The solid-concentration measuring apparatus 20 measures solid concentration Cr of the liquid toner retained in the toner tank 30 in the second embodiment. The solid-concentration measuring apparatus 20 is of basically the same configuration as the solid-concentration measuring apparatus 2 according to the first embodiment. The solid-concentration measuring apparatus 20 includes a solid-concentration measuring unit 201, a circulation pump 202, an ultrasonic transmitter 203, an ultrasonic sensor 204, a temperature sensor 205, a solid-concentration measurement control unit 206, and circulation tubes 207 and 208.

The solid-concentration measuring unit 201 is the same as the solid-concentration measuring unit 21 according to the first embodiment, and circulates a liquid toner supplied from the toner tank 30 between the ultrasonic transmitter 203 and the ultrasonic sensor 204. The solid-concentration measuring unit 201 communicates with the toner tank 30 through the circulation tubes 207 and 208.

The circulation pump 202 circulates the liquid toner between the toner tank 30 and the solid-concentration measuring unit 201. Drive or stop of the circulation pump 202 is controlled by, for example, the solid-concentration measurement control unit 206.

The ultrasonic transmitter 203 includes an impulse transducer (not shown) that transmits an ultrasonic wave, and a drive circuit that applies a transmission drive voltage to the impulse transducer. An ultrasonic-transmission controller 206d, explained later, of the solid-concentration measurement control unit 206 controls the ultrasonic transmitter 203 to transmit ultrasonic waves.

The ultrasonic sensor 204 is an ultrasonic receiver. The ultrasonic sensor 204 includes an impulse transducer (not shown) that receives ultrasonic waves. When receiving an ultrasonic wave, the ultrasonic sensor 204 outputs a received voltage to the solid-concentration measurement control unit 206.

The temperature sensor 205 is a temperature detector that detects a temperature Tr of the liquid toner in the toner tank 30. The detected temperature Tr of the liquid toner is output to the solid-concentration measurement control unit 206.

The solid-concentration measurement control unit 206 measures the solid concentration Cr of the liquid toner in the toner tank 30 by controlling the solid-concentration measuring apparatus 20. As shown in FIG. 9, the solid-concentration measurement control unit 206 includes an input-output (I/O) unit 206a, a processing unit 206b, and a memory unit 206c. The processing unit 206b includes the ultrasonic-transmission controller 206d, an ultrasonic receiver 206e, a pulse counter 206f, a response-time integrator 206g, a propagation-speed calculator 206h, and a concentration calculator 206i. It is noted that the solid-concentration measurement control unit 206 is connected to the supply-amount control unit 70, and the solid concentration Cr of the liquid toner in the toner tank 30 measured by the solid-concentration measuring apparatus 20 is output to the supply-amount control unit 70. The solid-concentration measurement control unit 206 drives the circulation pump 202 when an image forming apparatus 100 is operated.

The ultrasonic-transmission controller 206d causes the ultrasonic transmitter 203 to transmit each ultrasonic pulse.

The ultrasonic receiver 206e determines whether one ultrasonic pulse transmitted from the ultrasonic transmitter 203 has been received based on the received voltage of the ultrasonic pulse output to the solid-concentration measurement control unit 206 and received by the ultrasonic sensor 204.

The pulse counter 206f counts a pulse each time one ultrasonic pulse is transmitted from the ultrasonic transmitter 203.

The response-time integrator 206g measures a response time t for each pulse, the response time t being from transmission of one ultrasonic pulse by the ultrasonic transmitter 203 to reception of the transmitted one ultrasonic pulse by the ultrasonic sensor 204. The response-time integrator 206g integrates the measured response time t for each N pulses (N>1).

The propagation-speed calculator 206h is part of a concentration calculator. The propagation-speed calculator 206h calculates a propagation speed Sr of the ultrasonic wave from the ultrasonic transmitter 203 to the ultrasonic sensor 204, based on a propagation distance D from the ultrasonic transmitter 203 to the ultrasonic sensor 204, an integrated response time Xr which is a response time for N pulses integrated by the response-time integrator 206g, and the temperature Tr detected by the temperature sensor 205. In the second embodiment, the propagation-speed calculator 206h calculates the propagation speed Sr based on the integrated response time Xr and a temperature table (not shown) stored in the memory unit 206c. The temperature table has the same structure as that according to the first embodiment.

The concentration calculator 206i calculates a solid concentration Cr of the liquid toner in which solid content of a dilute solution, explained later, is added to a liquid containing solid content based on the integrated response time Xr or, in this case, the calculated propagation speed Sr. More specifically, the solid content of the dilute solution indicates the solid content most of which is formed with solid content from which particles containing colorants are removed, and the solid content contained in the liquid indicates the solid content of a concentrated liquid toner supplied from the conc. toner supply unit 40, that is, the solid content with the particles containing colorants. In the second embodiment, the concentration calculator 206i calculates the solid concentration Cr based on the propagation speed Sr and the solid concentration table stored in the memory unit 206c. The solid concentration table has the same structure as that of the first embodiment.

The toner tank 30 retains therein the liquid toner. The toner tank 30 is connected to the image forming apparatus 100 as shown in FIG. 8, and the retained liquid toner is appropriately supplied to the image forming apparatus 100.

The conc. toner supply unit 40 is a concentrated-liquid-toner supply unit. In the second embodiment, the conc. toner supply unit 40 supplies a concentrated liquid toner that contains more particles containing colorants, to the toner tank 30. More specifically, the concentrated liquid toner has an ideal solid concentration higher than that of the ordinary liquid toner, when a ratio of the particles containing colorants in the solid content is kept constant. The conc. toner supply unit 40 includes a conc. toner tank 41, a second pump 42, and a communicating tube 43. The conc. toner tank 41 retains therein previously supplied concentrated liquid toner.

The second pump 42 is a concentrated liquid toner pump, and supplies the concentrated liquid toner retained in the conc. toner tank 41 to the toner tank 30 through the communicating tube 43. The second pump 42 is connected to the supply-amount control unit 70 and is controlled by a second-pump controller 79, explained later, of the supply-amount control unit 70. The second-pump controller 79 controls the second pump 42 based on a control amount Pr of the second pump calculated by a second-pump control amount calculator 77, explained later. The second pump 42 is driven when the calculated control amount Pr is positive while it is not driven when negative.

The recycled-carrier supply unit 50 is a dilute-solution supply unit. The recycled-carrier supply unit 50 reuses the liquid toner as a dilute solution, retained in the toner tank 30. The liquid toner is such that the particles containing colorants are consumed by being used. More specifically, in the second embodiment, the recycled-carrier supply unit 50 supplies a dilute solution, which contains less particles containing colorants due to consumption by being used than that of the ordinary liquid toner but still contains residual material, to the toner tank 30. The recycled-carrier supply unit 50 includes a recycled-carrier tank 51, a first pump 52, a recycling unit 53, and communicating tubes 54, 55, and 56. The recycled-carrier tank 51 retains therein the dilute solution.

The first pump 52 is a dilute-solution pump, and supplies the dilute solution retained in the recycled-carrier tank 51 to the toner tank 30 through the communicating tube 56. The first pump 52 is connected to the supply-amount control unit 70, and is controlled by a first-pump controller 78, explained later, of the supply-amount control unit 70. The first-pump controller 78 controls the first pump 52 based on a control amount Pc of the first pump calculated by a first-pump control amount calculator 76 explained later. The first pump 52 is driven when the calculated control amount Pc is positive while it is not driven when negative. In the second embodiment, the first pump 52 has the same performance as that of the second pump 42.

The recycling unit 53 introduces thereto the liquid toner used in the image forming apparatus 100 and retained in the toner tank 30 through the communicating tube 54, and removes the particles containing colorants from the used liquid toner before the used liquid toner is introduced into the recycled-carrier tank 51 through the communicating tube 55. The method of removing the particles containing colorants contained in the liquid toner i.e., toner particles is implemented by the recycling unit 53 by arranging an electrode plate (not shown), when the toner particles are charged, charging the electrode plate to one polarity opposite to the polarity of the charged toner particles, and attracting the toner particles to the electrode plate.

The solid-concentration measuring apparatus 60 measures a solid-concentration equivalent Cc of the dilute solution stored in the recycled-carrier tank 51 in the second embodiment. The basic configuration of the solid-concentration measuring apparatus 60 is the same as that of the solid-concentration measuring apparatus 20, and includes a solid-concentration measuring unit 601, a circulation pump 602, an ultrasonic transmitter 603, an ultrasonic sensor 604, a temperature sensor 605, a solid-concentration measurement control unit 606, and circulation tubes 607 and 608.

The solid-concentration measuring unit 601 circulates the dilute solution supplied from the recycled-carrier tank 51 between the ultrasonic transmitter 603 and the ultrasonic sensor 604. The solid-concentration measuring unit 601 communicates with the recycled-carrier tank 51 through the circulation tubes 607 and 608.

The circulation pump 602 circulates the dilute solution between the recycled-carrier tank 51 and the solid-concentration measuring unit 601. Drive or stop of the circulation pump 602 is controlled by, for example, the solid-concentration measurement control unit 606.

The ultrasonic transmitter 603 includes an impulse transducer (not shown) that transmits an ultrasonic wave, and a drive circuit that applies a transmission drive voltage to the impulse transducer. An ultrasonic-transmission controller 606d, explained later, of the solid-concentration measurement control unit 606 controls the ultrasonic transmitter 603 to transmit ultrasonic waves.

The ultrasonic sensor 604 is an ultrasonic receiver. The ultrasonic sensor 604 includes an impulse transducer (not shown) that receives ultrasonic waves. When receiving an ultrasonic wave, the ultrasonic sensor 604 outputs a received voltage to the solid-concentration measurement control unit 606.

The temperature sensor 605 is a temperature detector that detects a temperature Tc of the dilute solution in the recycled-carrier tank 51. The detected temperature Tc of the dilute solution is output to the solid-concentration measurement control unit 606.

The solid-concentration measurement control unit 606 measures the solid-concentration equivalent Cc of the dilute solution in the recycled-carrier tank 51 by controlling the solid-concentration measuring apparatus 60. As shown in FIG. 10, the solid-concentration measurement control unit 606 includes an input-output (I/O) unit 606a, a processing unit 606b, and a memory unit 606c. The processing unit 606b includes an ultrasonic-transmission controller 606d, an ultrasonic receiver 606e, a pulse counter 606f, a response-time integrator 606g, a propagation-speed calculator 606h, and a concentration calculator 606i. It is noted that the solid-concentration measurement control unit 606 is connected to the supply-amount control unit 70, and outputs the solid-concentration equivalent Cc of the dilute solution in the recycled-carrier tank 51 measured by the solid-concentration measuring apparatus 60, to the supply-amount control unit 70. The solid-concentration measurement control unit 606 drives the circulation pump 602 when the image forming apparatus 100 is operated.

The ultrasonic-transmission controller 606d causes the ultrasonic transmitter 603 to transmit each ultrasonic pulse.

The ultrasonic receiver 606e determines whether one ultrasonic pulse transmitted from the ultrasonic transmitter 603 has been received based on the received voltage of the ultrasonic pulse output to the solid-concentration measurement control unit 606 and received by the ultrasonic sensor 604.

The pulse counter 606f counts a pulse each time one ultrasonic pulse is transmitted from the ultrasonic transmitter 603.

The response-time integrator 606g measures a response time t for each pulse, the response time t being from transmission of one ultrasonic pulse by the ultrasonic transmitter 603 to reception of the one ultrasonic pulse by the ultrasonic sensor 604. The response-time integrator 606g integrates the measured response time t for each N pulses (N>1).

The propagation-speed calculator 606h is part of a concentration calculator. The propagation-speed calculator 606h calculates a propagation speed Sc of the ultrasonic wave from the ultrasonic transmitter 603 to the ultrasonic sensor 604, based on a propagation distance Dc from the ultrasonic transmitter 603 to the ultrasonic sensor 604, an integrated response time Xr which is a response time for N pulses integrated by the response-time integrator 606g, and the temperature Tc detected by the temperature sensor 605. In the second embodiment, the propagation-speed calculator 606h calculates the propagation speed Sc based on the integrated response time Xc and a temperature table (not shown) stored in the memory unit 606c. The temperature table has the same structure as that according to the first embodiment.

The concentration calculator 606i calculates a solid-concentration equivalent Cc of the dilute solution which is a liquid toner with residual material that is solid content from which the particles containing colorants have been removed, based on the integrated response time Xc or, in this case, the calculated propagation speed Sc. More specifically, the liquid toner is one in which the particles containing colorants have decreased in such a manner that the liquid containing solid content or, in this case, the particles containing colorants have been consumed by the image forming apparatus 100 and have been further removed by the recycling unit 53. In the second embodiment, the concentration calculator 606i calculates the solid-concentration equivalent Cc based on the propagation speed Sc and a solid concentration table stored in the memory unit 606c. The solid concentration table has the same structure as that of the solid concentration table in the second embodiment.

The supply-amount control unit 70 is a supply-amount controller which controls the operation of the solid-concentration control system 1-2 that includes the solid-concentration measuring apparatuses 20 and 60. The supply-amount control unit 70 executes a solid-concentration control process to which is applied a solid-concentration measuring method. Input to the supply-amount control unit 70 are the solid concentration Cr of the liquid toner in the toner tank 30 measured by the solid-concentration measuring apparatus 20 for the liquid toner, the solid-concentration equivalent Cc of the dilute solution in the recycled-carrier tank 51 measured by the solid-concentration measuring apparatus 60 for the dilute solution, and a volume F of the liquid toner in the toner tank 30 measured by the toner-liquid-volume sensor 80. The supply-amount control unit 70 calculates a control amount Pc of the first pump 52 and a control amount Pr of the second pump 42 based on the input data, and controls the first pump 52 and the second pump 42 based on the calculated control amounts Pc and Pr, respectively.

That is, the supply-amount control unit 70 controls the supply of the concentrated liquid toner or of the dilute solution to the toner tank 30 based on the measured solid concentration Cr of the liquid toner in the toner tank 30, the measured solid-concentration equivalent Cc of the dilute solution in the recycled-carrier tank 51, and the measured volume F of the liquid toner in the toner tank 30. In the second embodiment, the supply-amount control unit 70 controls the first pump 52 and the second pump 42 based on the calculated respective control amounts Pc and Pr so that a differential solid concentration Cx between the solid concentration Cr and the solid-concentration equivalent Cc becomes a target ideal solid concentration Ct as a predetermined concentration and so that the volume F of the liquid toner becomes a target volume Ft of the liquid toner as a predetermined liquid volume.

Furthermore, as shown in FIG. 11, the supply-amount control unit 70 includes an input-output (I/O) unit 71, a processing unit 72, and a memory unit 73. The processing unit 72 is formed with a memory and a CPU. The processing unit 72 includes a target-value acquiring unit 74, a differential-solid-concentration calculator 75, the first-pump control amount calculator 76, the second-pump control amount calculator 77, the first-pump controller 78, and the second-pump controller 79.

The processing unit 72 can load a computer program into the memory and execute it to implement the solid-concentration control process to which is applied the solid-concentration measuring method. The memory unit 73 can be formed with a nonvolatile memory such as a flash memory, a memory that can only read data such as a ROM, or a memory that can read and write data such as a RAM, or a combination of these memories.

The target-value acquiring unit 74 acquires target values of the ideal solid concentration and the volume F of the liquid toner in the toner tank 30. In the second embodiment, the target-value acquiring unit 74 acquires a predetermined concentration which is the target ideal solid concentration Ct input by an input unit (not shown) connected to, for example, the supply-amount control unit 70, and also acquires a predetermined liquid volume which is the target volume Ft of the liquid toner.

The differential-solid-concentration calculator 75 calculates a difference between the solid concentration of the liquid toner in the toner tank 30 and the solid-concentration equivalent of the dilute solution in the recycled-carrier tank 51. In the second embodiment, the differential-solid-concentration calculator 75 calculates the difference, as a differential solid concentration Cx, between the solid concentration Cr of the liquid toner measured by the solid-concentration measuring apparatus 20 and the solid-concentration equivalent Cc of the dilute solution measured by the solid-concentration measuring apparatus 60.

The liquid toner retained in the toner tank 3 is a mixture of the concentrated liquid toner supplied by the conc. toner supply unit 40 and the dilute solution supplied by the recycled-carrier supply unit 50. More specifically, the solid content of the liquid toner in the toner tank 30 is such that the solid content of the dilute solution supplied from the recycled-carrier supply unit 50 or the residual material remaining after the particles containing colorants are consumed is added to the solid content of the concentrated liquid toner supplied from the conc. toner supply unit 40 or to the solid content with the particles containing colorants. In other words, the liquid toner in the toner tank, in which the concentrated liquid toner and the dilute solution are mixed, has a ratio of the particles containing colorants in the solid content smaller than a ratio of the particles containing colorants in the solid content of the concentrated liquid toner, even if the solid concentrations are the same as each other.

Therefore, the measured solid concentration Cr of the liquid toner in the toner tank 30 may deviate from the ideal solid concentration or the solid concentration of the liquid toner when the ratio of the particles containing colorants in the solid content of the liquid toner in the toner tank 30 or the ratio of the particles containing colorants in the solid content of the concentrated liquid toner is kept constant.

As a result, the differential-solid-concentration calculator 75 calculates a difference between the measured solid concentration Cr of the liquid toner and the measured solid-concentration equivalent Cc of the dilute solution, to determine the difference as a differential solid concentration. In other words, the differential-solid-concentration calculator 75 converts the solid concentration of the liquid toner in the toner tank 30 to the ideal solid concentration. More specifically, the liquid toner in the toner tank 30 is such that the residual material of the dilute solution supplied from the recycled-carrier supply unit 50 is added to the solid content of the concentrated liquid toner supplied from the conc. toner supply unit 40. The ideal solid concentration is the solid concentration of the liquid toner that contains only the solid content of the concentrated liquid toner supplied from the conc. toner supply unit 40. Consequently, the differential solid concentration Cx calculated by the differential-solid-concentration calculator 75 can be set as the ideal solid concentration of the liquid toner in the toner tank 30.

The differential-solid-concentration calculator 75 calculates the differential solid concentration Cx by using equation 1 as follows, where k is proportionality coefficient which is different depending on types of liquid toner such as colors used in the image forming apparatus 100. This is because the liquid toners of colors are different in each composition of particles containing colorants, and thus, their solid amount coefficient and solid amount constants are different from one another.

Equation 1

$$Cx = Cr - kCc \qquad (1)$$

The first-pump control amount calculator 76 calculates a control amount to control the first pump 52, for example, a rotational speed or the number of revolutions of the first pump 52. In the second embodiment, the first-pump control amount calculator 76 calculates a control amount Pc of the first pump 52 so that a concentration error $\Delta C(Ct-C(i))$ which is a difference between the target ideal solid concentration Ct and the differential solid concentration Cx decreases. The first-pump control amount calculator 76 calculates the control amount Pc of the first pump 52 as a value on the positive side so that the first pump 52 can be driven when the concentration error $\Delta C$ is negative or when the differential solid concentration Cx is higher than the target ideal solid concentration Ct. The control amount Pc of the first pump 52 is calculated by using the following equation 2, where K1 and K2 are integers for conversion to a control amount, and are coefficients for conversion to a rotational speed when the control amount Pc of the first pump 52 is, for example, the rotational speed.

Equation 2

$$Pc = -K1\sum_{i=1}^{n}(Ct - Cx(i)) + K2(Cx(i) - Cx(i-1)) \qquad (2)$$

In the equation 2, the control amount Pc of the first pump 52 is calculated by accumulating the concentration error $\Delta C$. If a discharge amount of the first pump 52 varies or if a defect occurs in supply of the dilute solution by the first pump 52 such that air is mixed into the dilute solution, the concentration error $\Delta C$ does not decrease, and the calculated control amount Pc continuously increases on the positive side. The supply amount of the dilute solution to the toner tank 30 by the first pump 52 thereby increases, which enables the concentration error $\Delta C$ to be speedily decreased. Furthermore, in the equation 2, the calculated control amount Pc decreases in association with the increase in a change amount (C(i)–C(i–1)) of the differential solid concentration Cx, and the supply amount of the dilute solution to the toner tank 30 by the first pump 52 thereby decreases. In other words, the first-pump control amount calculator 76 calculates the control amount Pc of the first pump 52 based on the change amount of the differential solid concentration Cx. With this feature, overshoot or undershoot in the control for the supply of the dilute solution can be suppressed.

The second-pump control amount calculator 77 calculates a control amount to control the second pump 42, for example, a rotational speed or the number of revolutions of the second pump 42. In the second embodiment, the second-pump control amount calculator 77 calculates a control amount Pr of the second pump 42 so that a concentration error $\Delta C$ which is a difference between the target ideal solid concentration Ct and the differential solid concentration Cx decreases, and so that a liquid volume error $\Delta F$ which is a difference between the target volume Ft of the liquid toner and the volume F of the liquid toner decreases. The second-pump control amount calculator 77 calculates the control amount Pr of the second pump 42 as a value on the positive side so that the second pump 42 can be driven when the concentration error $\Delta C$ is positive or when the differential solid concentration Cx is lower than the target ideal solid concentration Ct, and when the liquid volume error $\Delta F$ is positive or when the volume F of the liquid toner is lower than the target volume Ft of the liquid toner.

More specifically, the second-pump control amount calculator 77 calculates a concentration-error-based control amount Prc, which is a control amount of the second pump 42 based on the concentration error $\Delta C$ as a reference, and also calculates a liquid-volume-error-based control amount Prf, which is a control amount of the second pump 42 based on the liquid volume error $\Delta F$ as a reference. The second-pump control amount calculator 77 selects either the calculated concentration-error-based control amount Prc or liquid-volume-error-based control amount Prf, as the control amount Pr of the second pump 42.

The concentration-error-based control amount Prc is calculated by using the following equation 3 so that the concentration error $\Delta C$ decreases.

Equation 3

$$Prc = K1\sum_{i=1}^{n}(Ct - Cx(i)) - K2(Cx(i) - Cx(i-1)) \qquad (3)$$

In the equation 3, the concentration-error-based control amount Prc is calculated by accumulating the concentration error ΔC. If a discharge amount of the second pump 42 varies or if a defect occurs in supply of the concentrated liquid toner by the second pump 42 such that air is mixed into the concentrated liquid toner, the concentration error ΔC does not decrease, and the calculated concentration-error-based control amount Prc continuously increases on the positive side. The supply amount of the concentrated liquid toner to the toner tank 30 by the second pump 42 thereby increases, which enables the concentration error ΔC to be speedily decreased.

Furthermore, in the equation 3, the calculated concentration-error-based control amount Prc decreases in association with the increase in the change amount (C(i)–C(i–1)) of the differential solid concentration Cx, and the supply amount of the concentrated liquid toner to the toner tank 30 by the second pump 42 thereby decreases. In other words, the second-pump control amount calculator 77 calculates the concentration-error-based control amount Prc which is one of control amounts Pr of the second pump 42 based on the change amount of the differential solid concentration Cx. With this feature, overshoot or undershoot in the control for the supply of the concentrated liquid toner can be suppressed.

The liquid-volume-error-based control amount Prf is calculated by using the following equation 4 so that the liquid volume error ΔF decreases, where K3 and K3 are integers for conversion to a control amount, and are coefficients for conversion to a rotational speed when the liquid-volume-error-based control amount Prf which is one of the control amounts Pr of the second pump 42 is, for example, the rotational speed.

Equation 4

$$Prf = K3 \sum_{i=1}^{n} (Ft - F(i)) - K4(f(i) - F(i-1)) - Pc \quad (4)$$

In the equation 4, the liquid-volume-error-based control amount Prf is calculated by accumulating the liquid volume error ΔF. If a discharge amount of the second pump 42 varies or if a defect occurs in supply of the concentrated liquid toner by the second pump 42 such that air is mixed into the concentrated liquid toner, the liquid volume error ΔF does not decrease, and the calculated liquid-volume-error-based control amount Prf continuously increases on the positive side. The supply amount of the concentrated liquid toner to the toner tank 30 by the second pump 42 thereby increases, which enables the liquid volume error ΔF to be speedily decreased. Furthermore, in the equation 4, the calculated liquid-volume-error-based control amount Prf decreases in association with the increase in the change amount of the liquid toner in the toner tank 30 or in a measured change amount (F(i)–F(i–1)) of the volume F of the liquid toner, and the supply amount of the concentrated liquid toner to the toner tank 30 by the second pump 42 thereby decreases.

That is, the second-pump control amount calculator 77 calculates the liquid-volume-error-based control amount Prf which is one of the control amounts Pr of the second pump 42, based on the change amount of the measured volume F of the liquid toner. With this feature, overshoot or undershoot in the control for the supply of the concentrated liquid toner can be suppressed. Furthermore, in the equation 4, the control amount Pc of the first pump 52 is reduced. More specifically, the second pump 42 is controlled by the second-pump controller 79 based on the liquid-volume-error-based control amount Prf obtained by reducing the control amount Pc of the first pump 52 calculated so that the concentration error ΔC decreases.

The second-pump control amount calculator 77 selects either the concentration-error-based control amount Prc calculated based on the concentration error ΔC or the calculated liquid-volume-error-based control amount Prf, and sets the selected one as the control amount Pr of the second pump 42. More specifically, if the concentration error ΔC exceeds a predetermined value Cs, then the second-pump control amount calculator 77 selects the concentration-error-based control amount Prc and sets the selected one as the control amount Pr of the second pump 42. If the concentration error ΔC is the predetermined value Cs or less, then the second-pump control amount calculator 77 selects the liquid-volume-error-based control amount Prf and sets the selected one as the control amount Pr of the second pump 42.

That is, the second-pump control amount calculator 77 controls the second pump 42 based on the concentration-error-based control amount Prc when the concentration error ΔC exceeds the predetermined value Cs so that the concentration error ΔC decreases. Further, the second-pump control amount calculator 77 controls the second pump 42 based on the liquid-volume-error-based control amount Prf when the concentration error ΔC is the predetermined value Cs or less so that the liquid volume error ΔF decreases.

The first-pump controller 78 controls the first pump 52 based on the control amount Pc of the first pump calculated by the first-pump control amount calculator 76.

The second-pump controller 79 controls the second pump 42 based on the control amount Pr of the second pump calculated by the second-pump control amount calculator 77. More specifically, in the solid-concentration control system 1-2 according to the second embodiment, the first-pump controller 78 controls the supply of the dilute solution by controlling the first pump 52 based on the control amount Pc of the first pump 52, and the second-pump controller 79 controls the supply of the concentrated liquid toner by controlling the second pump 42 based on the control amount Pr of the second pump, so that the ideal solid concentration of the liquid toner in the toner tank 30 is made close to the target ideal solid concentration. In other words, the ideal solid concentration is controlled so as to reduce the concentration error ΔC, and the volume of liquid toner is controlled so as to reduce the liquid volume error ΔF, that is, the volume F of the liquid toner in the toner tank 30 is made close to the target volume Ft of the liquid toner.

The toner-liquid-volume sensor 80 is a liquid-volume measuring unit which measures a volume F of the liquid toner in the toner tank 30. The toner-liquid-volume sensor 80 is provided in the toner tank 30 and connected to the supply-amount control unit 70. The volume F of the liquid toner in the toner tank 30 measured by the toner-liquid-volume sensor 80 is output to the supply-amount control unit 70.

Figure 12:
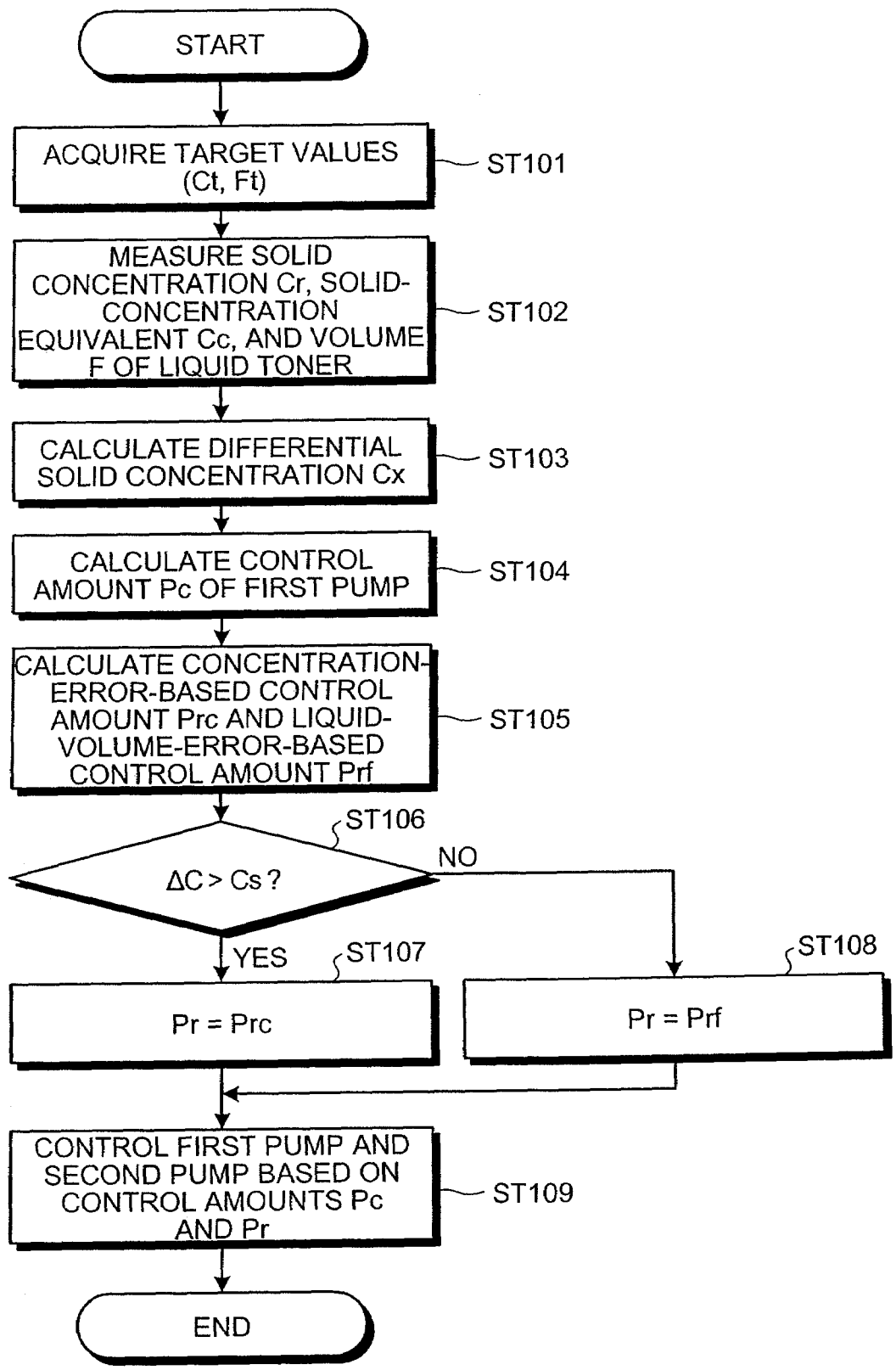
FIG. 12 is a flowchart of a solid-concentration control process according to the second embodiment.
Figure 13:
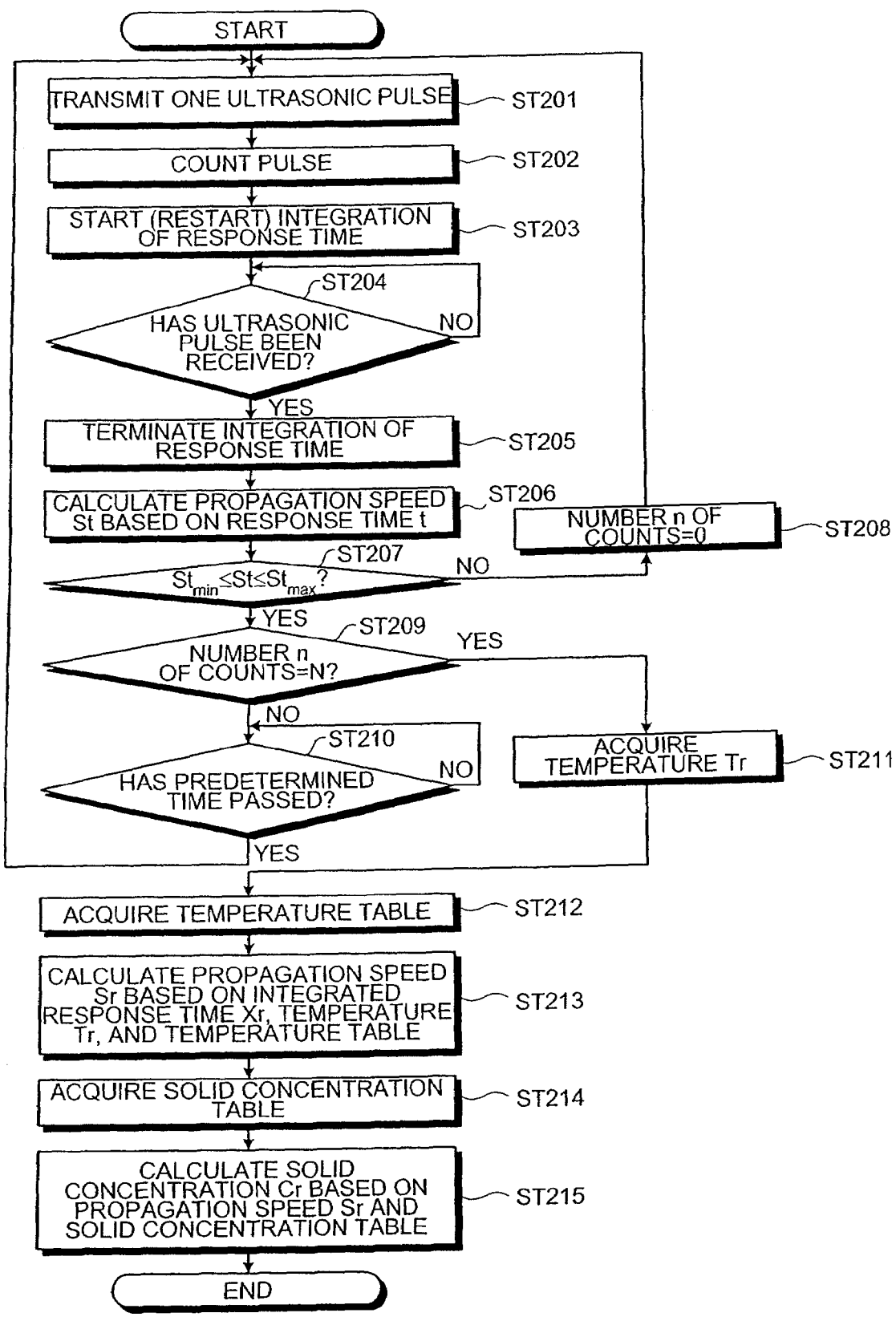
FIG. 13 is a flowchart of a solid-concentration measuring method for a liquid toner.
Figure 14:
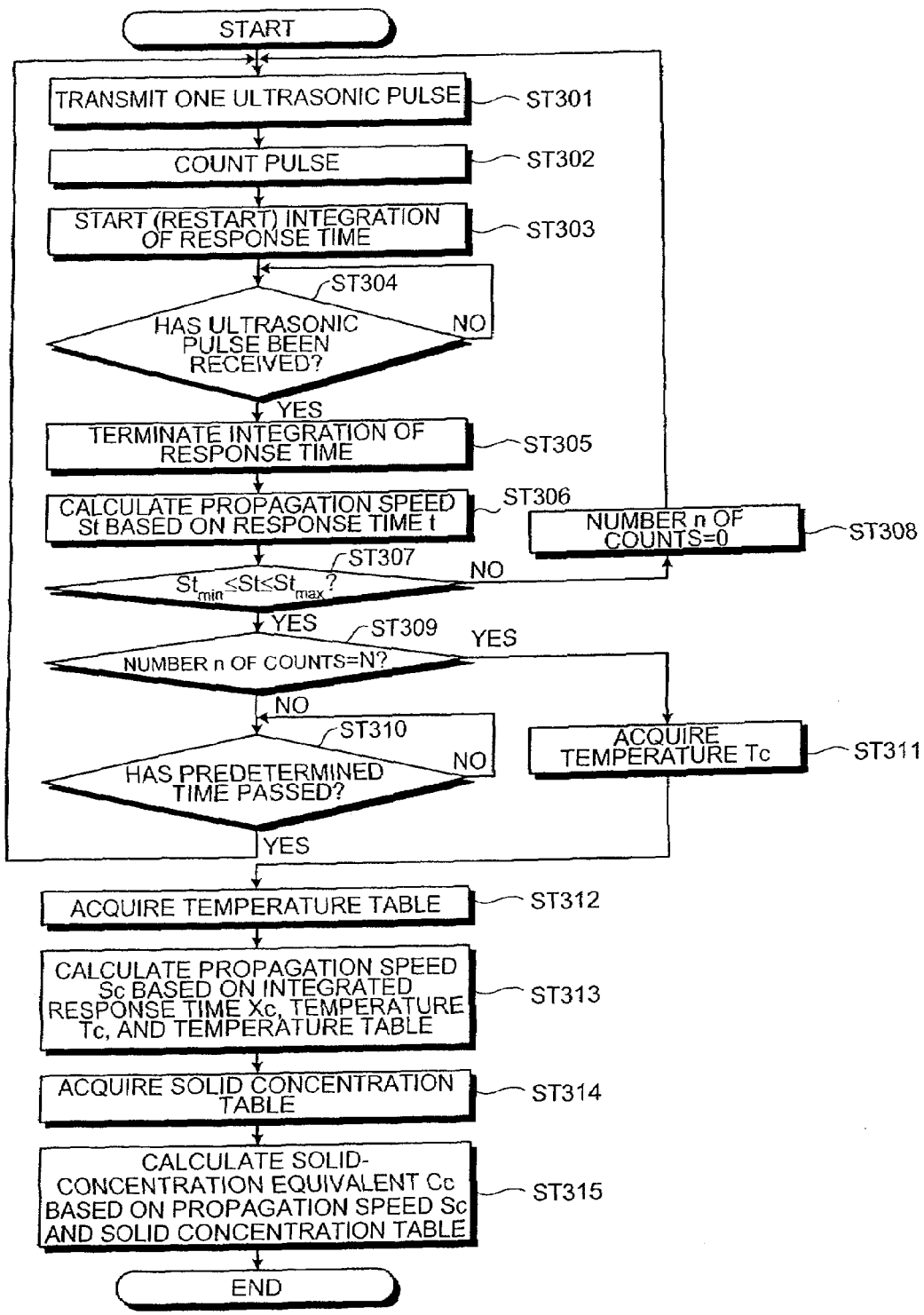
FIG. 14 is a flowchart of a solid-concentration measuring method for a dilute solution.

The operation of the solid-concentration control system 1-2 according to the second embodiment or the solid-concentration control process to which is applied the solid-concentration measuring method is explained below. FIG. 12 is a flowchart of the solid-concentration control process according to the second embodiment. FIG. 13 is a flowchart of the solid-concentration measuring method for a liquid toner. FIG. 14 is a flowchart of the solid-concentration measuring method for a dilute solution. It is noted that the basic procedure of the solid-concentration measuring method for the liquid toner shown in FIG. 13 and the solid-concentration measuring method for the dilute solution shown in FIG. 14 is the same as that of the solid-concentration measuring method according to the first embodiment as shown in FIG. 6. Thus, the basic procedure is omitted or is briefly explained below.

The target-value acquiring unit 74 of the processing unit 72 in the supply-amount control unit 70 acquires target values (Ct, Ft) (step ST101). The target-value acquiring unit 74 acquires, as target values, a target ideal solid concentration Ct which is a predetermined concentration and a target volume Ft of the liquid toner which is a predetermined liquid volume, both of which are input by, for example, an input unit and stored in the memory unit 73.

Next, the solid concentration Cr, the solid-concentration equivalent Cc, and the volume F of the liquid toner are measured (step ST102). Specifically, the solid-concentration measuring apparatus 20 measures the solid concentration Cr of the liquid toner in the toner tank 30, the solid-concentration measuring apparatus 60 measures the solid-concentration equivalent Cc of the dilute solution in the recycled-carrier tank 51, and the toner-liquid-volume sensor 80 measures the volume F of the liquid toner in the toner tank 30. The measured solid concentrations Cr and Cc and the measured volume F are output to the supply-amount control unit 70.

When the solid-concentration measuring apparatus 20 measures the solid concentration Cr of the liquid toner in the toner tank 30, the ultrasonic-transmission controller 206*d* of the processing unit 206*b* causes the ultrasonic transmitter 203 to transmit one ultrasonic pulse as shown in FIG. 13 (step ST201). The pulse counter 206*f* counts a pulse when the ultrasonic pulse is transmitted from the ultrasonic transmitter 203 (step ST202). The response-time integrator 206*g* starts integration of response time (step ST203). The ultrasonic receiver 206*e* determines whether the ultrasonic sensor 204 has received the ultrasonic pulse (step ST204). The response-time integrator 206*g* terminates the integration of the response time when it is determined that the ultrasonic receiver 206*e* has received the ultrasonic pulse (step ST205).

The response-time integrator 206*g* calculates one-pulse propagation speed St from the calculated response time t (step ST206). The response-time integrator 206*g* determines whether the calculated propagation speed St for each pulse is in a range from the minimum speed $St_{min}$ to the maximum speed $St_{max}$ (step ST207). When it is determined that the calculated propagation speed St for each pulse is not in the range, the pulse counter 206*f* sets the number n of counts to 0 (step ST208). When it is determined that the calculated propagation speed St for each pulse is in the range, the pulse counter 206*f* determines whether the number n of counts is N (step ST209).

When the pulse counter 206*f* determines that the number n of counts is not N, the ultrasonic-transmission controller 206*d* determines whether a predetermined time has passed from when it has been determined that the ultrasonic receiver 206*e* has received the ultrasonic pulse (step ST210). The integrated response time X, which is the response time integrated by the response-time integrator 206*g*, is the total of response times $t_1$ to $t_n$ from a first pulse to an n-th pulse each of which is a response time t in the liquid toner not containing air bubbles (see FIG. 7).

The propagation-speed calculator 206*h* acquires a temperature Tr when the pulse counter 206*f* determines that the number n of counts is N (step ST211). The propagation-speed calculator 206*h* acquires the temperature table (step ST212), and calculates the propagation speed Sr based on the integrated response time Xr, the temperature Tr, and the temperature table (step ST213).

Next, the concentration calculator 206*i* acquires the solid concentration table (step ST214), and calculates a solid concentration Cr based on the propagation speed Sr when the temperature is constant and the solid concentration table (step ST215). More specifically, the concentration calculator 206*i* which is the concentration measuring unit calculates the solid concentration Cr of the liquid toner based on the integrated response time X, that is, based on a propagation distance Dr and the integrated response time by using the solid concentration table. With these processes, the solid concentration Cr of the liquid toner in the toner tank 30 is measured by the solid-concentration measuring apparatus 20.

When the solid-concentration measuring apparatus 60 measures the solid-concentration equivalent Cc of the dilute solution in the recycled-carrier tank 51, the ultrasonic-transmission controller 606*d* of the processing unit 606*b* causes the ultrasonic transmitter 603 to transmit one ultrasonic pulse as shown in FIG. 14 (step ST301). The pulse counter 606*f* counts a pulse when the ultrasonic pulse is transmitted from the ultrasonic transmitter 603 (step ST302). The response-time integrator 606*g* starts integration of response time (step ST303). The ultrasonic receiver 606*e* determines whether the ultrasonic sensor 604 has received the ultrasonic pulse (step ST304).

The response-time integrator 606*g* terminates the integration of the response time when it is determined that the ultrasonic receiver 606*e* has received the ultrasonic pulse (step ST305). The response-time integrator 606*g* calculates one-pulse propagation speed St from the calculated response time t (step ST306). The response-time integrator 606*g* determines whether the calculated propagation speed St for each pulse is in a range from the minimum speed $St_{min}$ to the maximum speed $St_{max}$ (step ST307). When it is determined that the calculated propagation speed St for each pulse is not in the range, the pulse counter 606*f* sets the number n of counts to 0 (step ST308). When it is determined that the calculated propagation speed St for each pulse is in the range, the pulse counter 606*f* determines whether the number n of counts is N (step ST309).

When the pulse counter 606*f* determines that the number n of counts is not N, the ultrasonic-transmission controller 606*d* determines whether a predetermined time has passed from when it has been determined that the ultrasonic receiver 606*e* has received the ultrasonic pulse (step ST310). The integrated response time X, which is the response time integrated by the response-time integrator 606*g*, is the total of response times $t_1$ to $t_n$ from the first pulse to the n-th pulse each of which is the response time t in the liquid toner not containing air bubbles (see FIG. 7).

The propagation-speed calculator 606*h* acquires a temperature Tc when the pulse counter 606*f* determines that the number n of counts is N (step ST311). The propagation-speed calculator 606*h* acquires the temperature table (step ST312). The propagation-speed calculator 606*h* calculates the propagation speed Sc based on integrated response time Xc, the temperature Tc, and the temperature table (step ST313).

Next, the concentration calculator 606*i* acquires the solid concentration table (step ST314), and calculates a solid-concentration equivalent Cc based on the propagation speed Sc when the temperature is constant and the solid concentration table (step ST315). More specifically, the concentration calculator 606*i* which is the concentration measuring unit calculates the solid-concentration equivalent Cc of the dilute solution based on the integrated response time Xc, that is, based on the propagation distance Dc and the integrated response time by using the solid concentration table. With these processes, the solid-concentration equivalent Cc of the dilute solution in the recycled-carrier tank 51 is measured by the solid-concentration measuring apparatus 60.

As shown in FIG. 12, the differential-solid-concentration calculator 75 calculates a differential solid concentration Cx (step ST103). Specifically, the differential-solid-concentration calculator 75 calculates the differential solid concentration Cx, from the solid concentration Cr of the liquid toner which is measured by the solid-concentration measuring apparatus 20 and output to the supply-amount control unit 70, from the solid-concentration equivalent Cc of the dilute solution which is measured by the solid-concentration measuring apparatus 60 and output to the supply-amount control unit 70, and from the equation 1.

The first-pump control amount calculator 76 calculates the control amount Pc of the first pump 52 (step ST104). Specifically, the first-pump control amount calculator 76 calculates the control amount Pc of the first pump 52, from the acquired target ideal solid concentration Ct, the calculated differential solid concentration Cx, and from the equation 2. The control amount Pc of the first pump 52 is calculated as a value on the positive side when the concentration error $\Delta C$ is negative or when the differential solid concentration Cx is higher than the target ideal solid concentration Ct and when the ideal solid concentration of the liquid toner in the toner tank 30 is higher than the target ideal solid concentration Ct. The control amount Pc of the first pump 52 is calculated as a value on the negative side when the ideal solid concentration of the liquid toner is lower than the target ideal solid concentration Ct.

The second-pump control amount calculator 77 calculates the concentration-error-based control amount Prc and the liquid-volume-error-based control amount Prf (step ST105). Specifically, the second-pump control amount calculator 77 calculates the concentration-error-based control amount Prc which is one of the control amounts Pr of the second pump 42, from the acquired target ideal solid concentration Ct, the calculated differential solid concentration Cx, and from the equation 3. The concentration-error-based control amount Prc is calculated as a value on the positive side when the concentration error $\Delta C$ is positive or when the differential solid concentration Cx is lower than the target ideal solid concentration Ct and when the ideal solid concentration of the liquid toner in the toner tank 30 is lower than the target ideal solid concentration Ct. The concentration-error-based control amount Prc is calculated as a value on the negative side when the ideal solid concentration of the liquid toner is higher than the target ideal solid concentration Ct.

The second-pump control amount calculator 77 calculates a concentration-error-based control amount Prf, which is one of the control amounts Pr of the second pump 42, from the target volume Ft of the liquid toner acquired by the target-value acquiring unit 74, from the volume F of the liquid toner measured by the toner-liquid-volume sensor 80 and output to the supply-amount control unit 70, from the control amount Pc of the first pump 52 calculated by the first-pump control amount calculator 76, and from the equation 4. The liquid-volume-error-based control amount Prf is calculated as a value on the positive side when the liquid volume error $\Delta F$ is positive or when the volume F of the liquid toner in the toner tank 30 is lower than the target volume Ft of the liquid toner, and is calculated as a value on the negative side when the volume F of the liquid toner is higher than the target volume Ft of the liquid toner.

The second-pump control amount calculator 77 determines whether the concentration error $\Delta C$ exceeds a predetermined value Cs (step ST106). Specifically, the second-pump control amount calculator 77 determines whether the concentration error $\Delta C$ i.e., the ideal solid concentration of the liquid toner in the toner tank 30 exceeds the predetermined value Cs. The predetermined value Cs indicates an ideal solid concentration with which an image is not caused to be wet when the image forming apparatus 100 forms the image on a recording medium using the liquid toner in the toner tank 30.

When it is determined that the concentration error $\Delta C$ exceeds the predetermined value Cs, the second-pump control amount calculator 77 sets the concentration-error-based control amount Prc as the control amount Pr (=Prc) of the second pump 42 (step ST107).

When it is determined that the concentration error $\Delta C$ is the predetermined value Cs or less, the second-pump control amount calculator 77 sets the liquid-volume-error-based control amount Prf as the control amount Pr (=Prf) of the second pump 42 (step ST108).

The first-pump controller 78 controls the first pump 52 based on the control amount Pc of the first pump 52, and the second-pump controller 79 controls the second pump 42 based on the control amount Pr of the second pump 42 (step ST109). Consequently, the first pump 52 and the second pump 42 are controlled by the first-pump controller 78 and the second-pump controller 79 based on the control amount PC and the control amount Pr, respectively. Basically, when the ideal solid concentration of the liquid toner in the toner tank 30 is higher than the target ideal solid concentration Ct, the control amount Pc of the first pump 52 becomes a value on the positive side while the control negative side. In this case, only the first pump 52 is driven and the dilute solution is supplied from the recycled-carrier supply unit 50 to the toner tank 30 so that the ideal solid concentration of the liquid toner in the toner tank 30 decreases.

On the other hand, when the ideal solid concentration of the liquid toner in the toner tank 30 is lower than the target ideal solid concentration Ct, the control amount Pc of the first pump 52 becomes a value on the negative side while the control amount Pr of the second pump 42 becomes a value on the positive side. In this case, only the second pump 42 is driven and the concentrated liquid toner is supplied from the conc. toner supply unit 40 to the toner tank 30 so that the ideal solid concentration of the liquid toner in the toner tank 30 increases. Furthermore, when the volume F of the liquid toner in the toner tank 30 is less than the target volume Ft of the liquid toner, the control amount Pr of the second pump 42 becomes a value on the positive side. Therefore, the second pump 42 is driven to supply the concentrated liquid toner from the conc. toner supply unit 40 to the toner tank 30, and the volume of the liquid toner in the toner tank 30 thereby increases.

As explained above, in the solid-concentration control system 1-2 according to the second embodiment, the supply of the concentrated liquid toner and the dilute solution is controlled so that the concentration error $\Delta C$ between the target ideal solid concentration Ct and the differential solid concentration Cx decreases, and is controlled so that the liquid volume error $\Delta F$ between the target volume Ft of the liquid toner and the measured volume F of the liquid toner decreases. As explained above, because the differential solid concentration Cx calculated by the differential-solid-concentration calculator 75 is the ideal solid concentration of the liquid toner in the toner tank 30, the supply of the concentrated liquid toner can be controlled so that the ideal solid concentration of the liquid toner in the toner tank 30 is set as the target ideal solid concentration Ct which is the predetermined concentration, and the supply of the dilute solution can be controlled so that the volume F of the liquid toner is set as the target volume Ft of the liquid toner which is the predetermined liquid volume.

Therefore, in addition to the effect of the solid-concentration control system 1-1 according to the first embodiment, the supply-amount control unit 70 can supply the liquid toner with the target ideal solid concentration Ct to the image forming apparatus 100 even if the measured solid concentration Cr of the liquid toner deviates from the ideal solid concentration by controlling the supply of the concentrated liquid toner or of the dilute solution so that the differential solid concentration Cx becomes the target ideal solid concentration Ct. Moreover, the ideal solid concentration of the liquid toner in the toner tank 30 can be set as a desired ideal solid concentration or as the target ideal solid concentration Ct, and the volume F of the liquid toner in toner tank 30 can be set as a desired volume of liquid toner or as the target volume Ft of the liquid toner. With these features, the liquid toner with the target ideal solid concentration Ct can be stably supplied to the image forming apparatus 100.

Furthermore, when the concentration error ΔC exceeds the predetermined value Cs or when the concentration error ΔC is large, the ideal solid concentration of the liquid toner in the toner tank 30 which is the differential solid concentration Cx is set to the desired ideal solid concentration or to the target ideal solid concentration Ct and then the volume F of the liquid toner in the toner tank 30 is set to the desired volume of the liquid toner or to the target volume Ft of the liquid toner. With these features, it is possible to increase the volume of the liquid toner in the toner tank 30 while maintaining the solid concentration of the liquid toner as the target ideal solid concentration Ct. Consequently, a large amount of the liquid toner with the target ideal solid concentration Ct can be supplied to the image forming apparatus 100, which enables the image forming apparatus 100 to operate for a long time.

When there is the liquid volume error ΔF and the concentration error ΔC exceeds the predetermined value Cs, the second pump 42 is controlled by the liquid-volume-error-based control amount Prf in which the calculated control amount Pc of the first pump 52 has been reduced so that the concentration error ΔC being the control amount Pr of the second pump 42 decreases. Therefore, even if the control of the ideal solid concentration and the control of the volume of the liquid toner are concurrently provided, it is possible to suppress the changes in the ideal solid concentration and the volume of the liquid toner in the toner tank 30 due to the mutual controls, by controlling the first pump 52 and the second pump 42 so that the concentration error ΔC and the liquid volume error ΔF decrease. In short, when the ideal solid concentration and the volume of the liquid toner are concurrently controlled, mutual interference with the controls can be minimized. Accordingly, making the liquid toner in the toner tank 30 to the target ideal solid concentration Ct and making the volume of liquid toner to the target volume Ft of the liquid toner can be concurrently and rapidly performed.

As set forth hereinabove, according to an embodiment of the present invention, it is possible to improve accuracy in the measurement of solid concentration of liquid containing solid content.

Specifically, the solid concentration of the liquid containing solid content or a ratio of the solid concentration to the liquid is almost proportional to the response time or to the propagation speed obtained from the response time and the propagation distance. In other words, the solid concentration changes according to the change in the response time or the propagation speed. According to an embodiment of the present invention, the solid concentration can be calculated based on the integrated response time obtained by integrating the response time, for N pulses, from transmission of a single-pulse ultrasonic wave by the ultrasonic transmitter such as the impulse transducer for transmission to its reception by the ultrasonic receiver such as the impulse transducer for reception. Alternatively, the solid concentration can be calculated based on the propagation speed calculated based on the propagation distance and the integrated response time. Therefore, the influence of the disturbances does not have to be considered when the solid concentration of the liquid containing the solid content is measured by using the conventional optical sensor, which enables measurement precision of the solid concentration of the liquid containing the solid content to be improved.

As explained above, the response time changes with the change in the solid concentration of the liquid containing the solid content. The change amount of the response time according to the change in the solid concentration becomes a slight amount because the response time decreases when the propagation distance of the ultrasonic wave is short. Therefore, when the propagation distance is short, a slight amount of change in a short response time or a minute time needs to be precisely measured, which makes it difficult to improve the measurement precision of the concentration. According to an embodiment of the present invention, however, the solid concentration is calculated based on the integrated response time obtained by integrating the response time, for N pulses, from transmission of a single-pulse ultrasonic wave by the ultrasonic transmitter to its reception by the ultrasonic receiver. Therefore, when the solid concentration changes, the change amount of the integrated response time becomes N times of the change amount of the response time, and thus, the change in the integrated response time can be more precisely measured than the change in the response time. Accordingly, even if the propagation distance is short, it is possible to improve the measurement precision of the solid concentration of the liquid containing the solid content.

The sound speed in the liquid is almost proportional to the temperature of the liquid. In other words, the sound speed in the liquid changes as the temperature changes. Because the propagation speed of the ultrasonic wave in the liquid containing the solid content changes according to the temperature of the liquid, when the temperatures are different even if the integrated response time is not changed, the calculated solid concentrations are different from each other. According to an embodiment of the present invention, however, the solid concentration to be calculated is corrected according to the change in the detected temperature. For example, when the solid concentration is to be calculated, the propagation speed, from which the change amount in the sound speed in the liquid due to the temperature change is removed, is calculated based on the propagation distance, the integrated response time, and the detected temperature, and the solid concentration is calculated based on the calculated propagation speed. Therefore, even if the temperature changes during measurement of the solid concentration, it can be suppressed that the calculated solid concentration is different from an actual concentration. Thus, the measurement precision of the solid concentration of the liquid containing the solid content can further be improved.

The liquid sometimes contains air bubbles. Because the sound speed is largely different in the liquid and in the gas, the sound speed in the liquid largely changes depending on whether the air bubbles are contained therein. Therefore, the propagation speed of the ultrasonic wave when the liquid contains the air bubbles is different from that when the liquid does not contain the air bubbles. According to an embodiment of the present invention, of propagation speeds of each pulse based on the response time from transmission of a single-pulse ultrasonic wave by the ultrasonic transmitter to its reception, the propagation speed of each pulse based on a response time as follows is not integrated, that is, this propagation speed is not used for calculation of the solid concentration. The response time is the time from transmission of a single-pulse ultrasonic wave by the ultrasonic transmitter to its reception, which is outside the predetermined range, or which is outside the range of the propagation speed of the ultrasonic wave in the liquid not containing air bubbles but containing solid content. Therefore, even if the air bubbles are contained in the liquid containing the solid content during measurement of its solid concentration, it can be suppressed that the calculated solid concentration is different from an actual concentration. Thus, the measurement precision of the solid concentration of the liquid containing the solid content can further be improved.

Moreover, according to an embodiment of the present invention, the solid-concentration control system can easily maintain the solid concentration to a predetermined concentration because the solid concentration of the liquid toner measured by the solid-concentration measuring apparatus i.e., a ratio of the solid content with particles containing colorants to the liquid toner is measured highly precisely. Therefore, the liquid toner with a desired solid concentration can be supplied to an image forming apparatus.

When the liquid toner, in which the particles or the like containing colorants have been consumed by being used, is reused as a dilute solution, a residual material other than the particles containing colorants is still contained in the dilute solution. The residual material affects the propagation speed of the ultrasonic wave. Therefore, when the dilute solution is supplied to the toner tank, the solid content of the liquid toner in the toner tank becomes a solid content in which the residual material of the dilute solution is added to the solid content of the concentrated liquid toner supplied from the concentrated-liquid-toner supply unit or added to the solid content with the particles containing colorants. More specifically, even if the liquid toner in the toner tank into which the concentrated liquid toner and the dilute solution are a ratio of the particles containing colorants in the solid content of the liquid toner in the toner tank into which the dilute solution is supplied is smaller than a ratio of the particles containing colorants in the solid content of the concentrated liquid toner. Consequently, the measured solid concentration of the liquid toner may possibly deviate from the ideal solid concentration or from the solid concentration of the liquid toner when the ratio of the particles containing colorants in the solid content of the liquid toner in the toner tank is constant.

According to an embodiment of the present invention, however, the differential solid concentration is a difference between the measured solid concentration of the liquid toner and the measured solid-concentration equivalent of the dilute solution. Therefore, the differential solid concentration is the ideal solid concentration when the ratio of the particles containing colorants in the solid content of the liquid toner in the toner tank is constant. Consequently, the supply-amount controller controls the supply of at least either one of the concentrated liquid toner and the dilute solution so that the differential solid concentration becomes the predetermined concentration, and the liquid toner with a desired ideal solid concentration can thereby be supplied to an image forming apparatus even if the measured solid concentration of the liquid toner deviates from the ideal solid concentration.

Although the invention has been described with respect to a specific embodiment for a complete and clear disclosure, the appended claims are not to be thus limited but are to be construed as embodying all modifications and alternative constructions that may occur to one skilled in the art that fairly fall within the basic teaching herein set forth.

What is claimed is:

1. A solid-concentration control system comprising:
    a toner tank that is configured to contain a liquid toner including color particles as solid content and silicone oil as a carrier liquid;
    a first supply unit that supplies a concentrated liquid toner to the toner tank;
    a second supply unit that supplies a dilute solution including silicone oil to the toner tank, the dilute solution further including a used liquid toner from which at least some of the color particles have been consumed;
    a supply controller that controls supply of at least one of the concentrated liquid toner and the dilute solution to the toner tank;
    a first solid-concentration measuring apparatus that measures a first solid concentration of the liquid toner contained in the toner tank; and
    a second solid-concentration measuring apparatus that measures a second solid concentration of the dilute solution supplied by the second supply unit, wherein
    each of the first and second solid-concentration measuring apparatuses includes
    an ultrasonic transmitter that transmits a single-pulse ultrasonic wave to the liquid toner or the dilute solution;
    an ultrasonic receiver that faces the ultrasonic transmitter through the liquid toner or the dilute solution, and that receives the single-pulse ultrasonic wave;
    an ultrasonic-transmission controller that controls the ultrasonic transmitter to transmit another single-pulse ultrasonic wave after a predetermined time has passed after the ultrasonic receiver receives the single-pulse ultrasonic wave;
    a response-time integrator that measures a response time from transmission to reception of each single-pulse ultrasonic wave, and integrates measured response time with respect to each set of N pulses, N being an integer larger than 1; and
    a concentration calculator that calculates the first or second solid concentration based on integrated response time, and
    the supply controller controls the supply to the toner tank based on a differential solid concentration, which is a difference between the first and second solid concentrations, to adjust the solid concentration to a predetermined concentration.

2. The solid-concentration control system according to claim 1, wherein the concentration calculator calculates a propagation speed of the single-pulse ultrasonic wave from the ultrasonic transmitter to the ultrasonic receiver based on a propagation distance from the ultrasonic transmitter to the ultrasonic receiver and the integrated response time, and calculates the first or second solid concentration based on the calculated propagation speed.

3. The solid-concentration control system according to claim 2, wherein the response-time integrator integrates a response time from transmission to reception of a single-pulse ultrasonic wave only when a propagation speed of the single-pulse ultrasonic wave derived from the response time is in a predetermined range.

4. The solid-concentration control system according to claim 1, wherein the predetermined time is a time period from transmission of a single-pulse ultrasonic wave until the ultrasonic receiver receives no reverberation of the single-pulse ultrasonic wave.

5. The solid-concentration control system according to claim 4, wherein the response-time integrator integrates a response time from transmission to reception of a single-pulse ultrasonic wave only when a propagation speed of the single-pulse ultrasonic wave derived from the response time is in a predetermined range.

6. The solid-concentration control system according to claim 1, wherein at least one of the first and second solid-concentration measuring apparatuses further comprises a temperature detector that detects a temperature of the liquid toner or the dilute solution, wherein
the concentration calculator corrects the calculated first or second solid concentration according to a change in the detected temperature.

7. The solid-concentration control system according to claim 6, wherein the concentration calculator calculates a propagation speed of the single-pulse ultrasonic wave from the ultrasonic transmitter to the ultrasonic receiver based on a propagation distance from the ultrasonic transmitter to the ultrasonic receiver, the integrated response time, and detected temperature, and calculates the first or second solid concentration based on the calculated propagation speed.

8. The solid-concentration control system according to claim 6, wherein the response-time integrator integrates a response time from transmission to reception of a single-pulse ultrasonic wave only when a propagation speed of the single-pulse ultrasonic wave derived from the response time is in a predetermined range.

9. The solid-concentration control system according to claim 1, wherein the ultrasonic transmitter and the ultrasonic receiver include an impulse transducer.

10. The solid-concentration control system according to claim 1, further comprising a liquid-volume measuring unit that measures a volume of the liquid toner contained in the toner tank, wherein
the supply controller controls the supply to the toner tank further based on measured volume of the liquid toner to adjust the volume of the liquid toner to a predetermined liquid volume.

11. The solid-concentration control system according to claim 10, wherein
the first supply unit includes a first pump that supplies the concentrated liquid toner to the toner tank,
the second supply unit includes a second pump that supplies the dilute solution to the toner tank, and
the supply controller calculates a control amount of the first pump and a control amount of the second pump to minimize concentration error between the predetermined concentration and the differential solid concentration and liquid-volume error between the predetermined liquid volume and the measured volume of the liquid toner, and controls the first pump and the second pump based on calculated control amounts.

12. The solid-concentration control system according to claim 11, wherein the supply controller calculates the control amount of at least one of the first pump and the second pump based on at least one of a change amount of the differential solid concentration and a change amount of the measured volume of the liquid toner.

13. The solid-concentration control system according to claim 11, wherein
the supply controller calculates a first control amount based on the concentration error, and controls the first pump, when the concentration error exceeds a predetermined threshold, to minimize the concentration error based on the first control amount, and
the supply controller calculates a second control amount based on the liquid-volume error, and controls the first pump, when the concentration error is equal to or less than the predetermined threshold, to minimize the liquid-volume error based on the second control amount.

14. The solid-concentration control system according to claim 13, wherein the second control amount is obtained by reducing the control amount of the second pump calculated to minimize the concentration error.

15. A solid-concentration control method comprising:
containing in a toner tank a liquid toner including color particles as solid content and silicone oil as a carrier liquid;
supplying from a first supply unit a concentrated liquid toner to the toner tank;
supplying from a second supply unit a dilute solution including silicone oil to the toner tank, the dilute solution further including a used liquid toner from which at least some of the color particles have been consumed;
controlling at a supply controller supply of at least one of the concentrated liquid toner and the dilute solution to the toner tank; and
measuring at a first solid-concentration measuring apparatus a first solid concentration of the liquid toner contained in the toner tank and at a second solid-concentration measuring apparatus a second solid concentration of the dilute solution supplied from the second supply unit, wherein the measuring includes:
transmitting from an ultrasonic transmitter a first single-pulse ultrasonic wave to the liquid toner or the dilute solution;
receiving at an ultrasonic receiver the first single-pulse ultrasonic wave;
transmitting a second single-pulse ultrasonic wave after a predetermined time has passed from receipt of the first single-pulse ultrasonic wave;
measuring a response time from transmission to reception of each single-pulse ultrasonic wave;
integrating measured response time with respect to each set of N pulses, N being an integer larger than 1; and
calculating the first or second solid concentration based on integrated response time, and the controlling includes controlling the supply to the toner tank based on a differential solid concentration which is a difference between the first and second solid concentrations to adjust the differential solid concentration to a predetermined concentration.

16. The solid-concentration control method according to claim 15, further comprising determining whether a predetermined time has passed from receiving the first single-pulse ultrasonic wave before transmitting the second single-pulse ultrasonic wave.

17. The solid-concentration control method according to claim 16, wherein the predetermined time is a time from when the first single-pulse ultrasonic wave until the ultrasonic receiver receives no more reverberations of at least one transmitted ultrasonic pulse.

* * * * *